(12) United States Patent
Hwang et al.

(10) Patent No.: US 11,342,507 B2
(45) Date of Patent: May 24, 2022

(54) COATING COMPOSITION COMPRISING COMPOUND, AND ORGANIC LIGHT EMITTING DEVICE COMPRISING SAME

(71) Applicant: LG Chem, Ltd., Seoul (KR)

(72) Inventors: Minho Hwang, Daejeon (KR); Esder Kang, Daejeon (KR); Hwakyung Kim, Daejeon (KR); Jaesoon Bae, Daejeon (KR); Hyeonah Shin, Daejeon (KR); Soyoung Yu, Daejeon (KR); Jaechol Lee, Daejeon (KR); Sejin Jung, Daejeon (KR)

(73) Assignee: LG Chem, Ltd.

( * ) Notice: Subject to any disclaimer, the term of this patent is extended or adjusted under 35 U.S.C. 154(b) by 746 days.

(21) Appl. No.: 16/328,495

(22) PCT Filed: Jun. 1, 2018

(86) PCT No.: PCT/KR2018/006286
§ 371 (c)(1),
(2) Date: Feb. 26, 2019

(87) PCT Pub. No.: WO2019/009521
PCT Pub. Date: Jan. 10, 2019

(65) Prior Publication Data
US 2019/0189926 A1    Jun. 20, 2019

(30) Foreign Application Priority Data

Jul. 7, 2017  (KR) .................. 10-2017-0086663

(51) Int. Cl.
*H01L 51/50* (2006.01)
*H01L 51/00* (2006.01)
(Continued)

(52) U.S. Cl.
CPC ............ *H01L 51/0059* (2013.01); *C09D 4/00* (2013.01); *H01L 51/0003* (2013.01); *H01L 51/0058* (2013.01); *H01L 51/52* (2013.01); *H01L 51/56* (2013.01); *C07C 211/54* (2013.01); *C07C 309/35* (2013.01); *H01L 51/006* (2013.01); *H01L 51/0022* (2013.01);
(Continued)

(58) Field of Classification Search
None
See application file for complete search history.

(56) References Cited

U.S. PATENT DOCUMENTS 6,001,934 A     12/1999   Yamanaka et al.
2004/0067387 A1  4/2004   Kim et al.
(Continued)

FOREIGN PATENT DOCUMENTS

EP     3101003 A1    12/2016
KR     20040028954 A  4/2004
(Continued)

OTHER PUBLICATIONS

Search report from International Application No. PCT/KR2018/006286, dated Sep. 7, 2018.

*Primary Examiner* — Gregory D Clark
(74) *Attorney, Agent, or Firm* — Lerner, David, Littenberg, Krumholz & Mentlik, LLP

(57) ABSTRACT

The present specification relates to a coating composition comprising a compound, and an organic light emitting device comprising the same.

14 Claims, 4 Drawing Sheets

(51) Int. Cl.
  *H01L 51/56*   (2006.01)
  *C09D 4/00*    (2006.01)
  *H01L 51/52*   (2006.01)
  C07C 309/35    (2006.01)
  C07C 211/54    (2006.01)

(52) U.S. Cl.
  CPC ...... *H01L 51/0054* (2013.01); *H01L 51/0094* (2013.01); *H01L 51/5056* (2013.01); *H01L 51/5088* (2013.01); *H01L 2251/308* (2013.01)

(56) References Cited

U.S. PATENT DOCUMENTS

| | | |
|---|---|---|
| 2008/0029742 A1 | 2/2008 | Yoshimoto et al. |
| 2010/0320422 A1 | 12/2010 | Nakane et al. |
| 2011/0195355 A1 | 8/2011 | Nakaie et al. |
| 2014/0227815 A1 | 8/2014 | Nakaie et al. |

FOREIGN PATENT DOCUMENTS

| | | | | |
|---|---|---|---|---|
| KR | 20070051288 A | | 5/2007 | |
| KR | 20090125516 A | | 12/2009 | |
| KR | 2009-125516 | * | 6/2010 | ............. C08G 65/26 |
| KR | 20100119876 A | | 11/2010 | |
| KR | 20140065441 A | | 5/2014 | |
| KR | 20150143574 A | | 12/2015 | |
| WO | 2010041701 A1 | | 4/2010 | |
| WO | 2015115515 A1 | | 8/2015 | |

* cited by examiner

【FIG. 1】
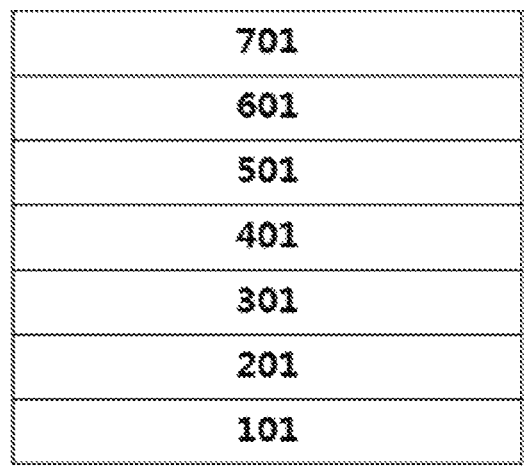
【FIG. 2】
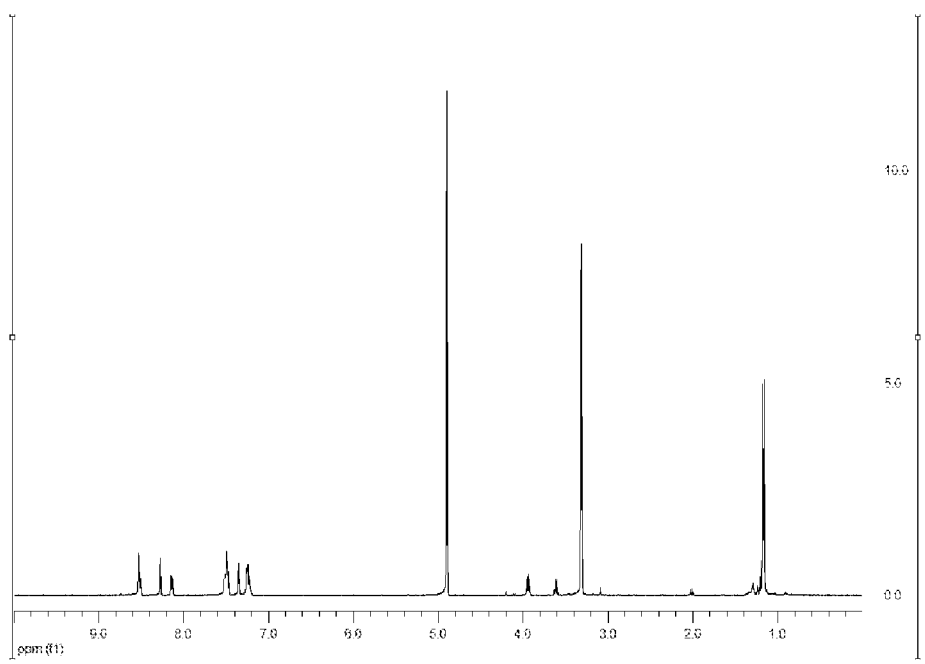

【FIG. 3】
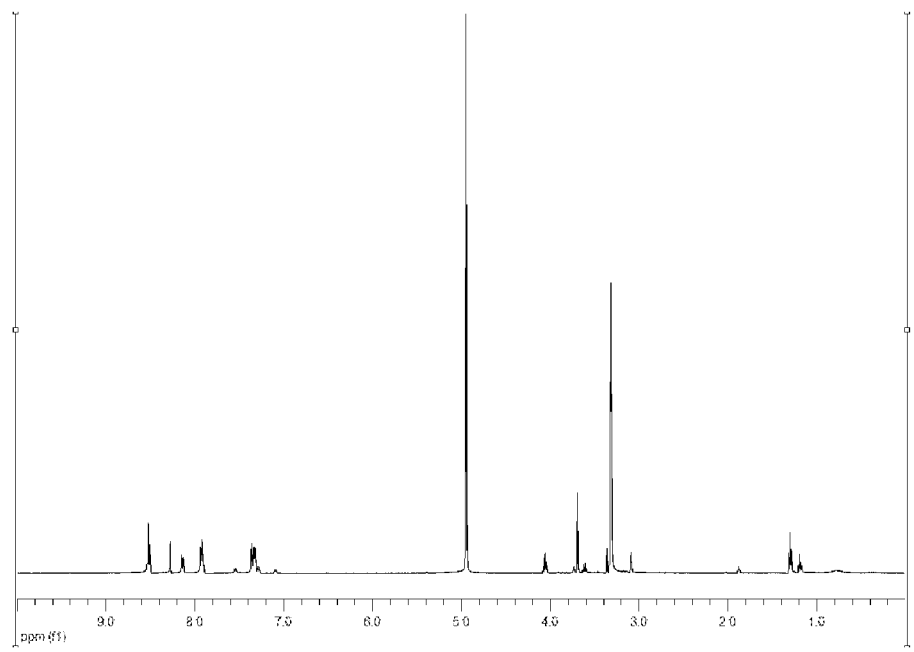
【FIG. 4】
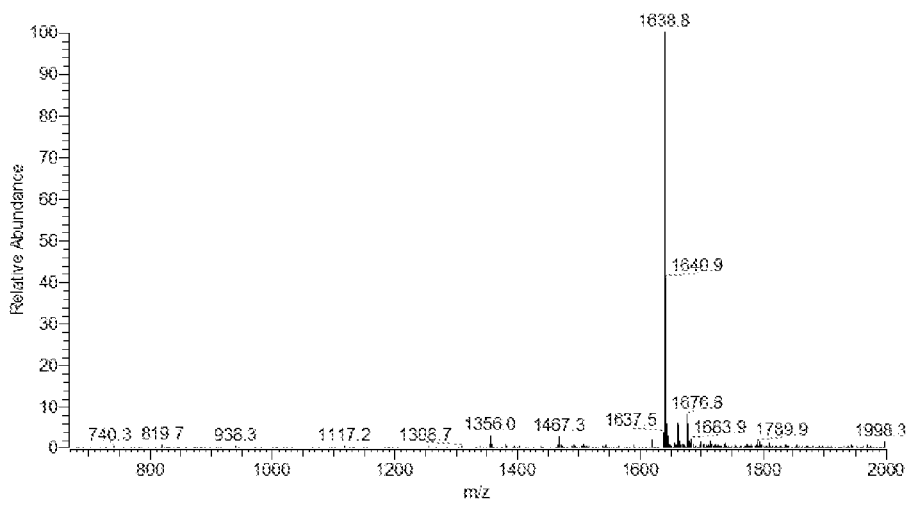

[FIG. 5]
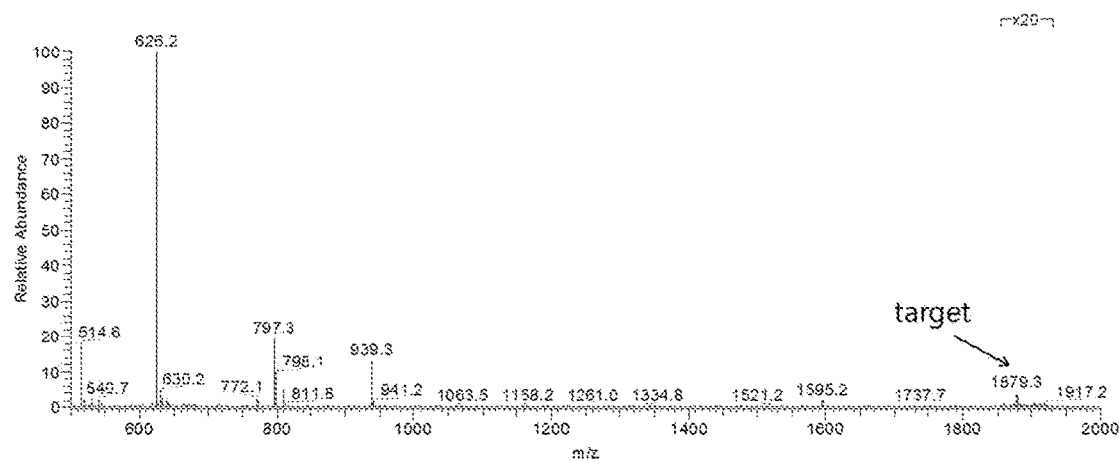
[FIG. 6]
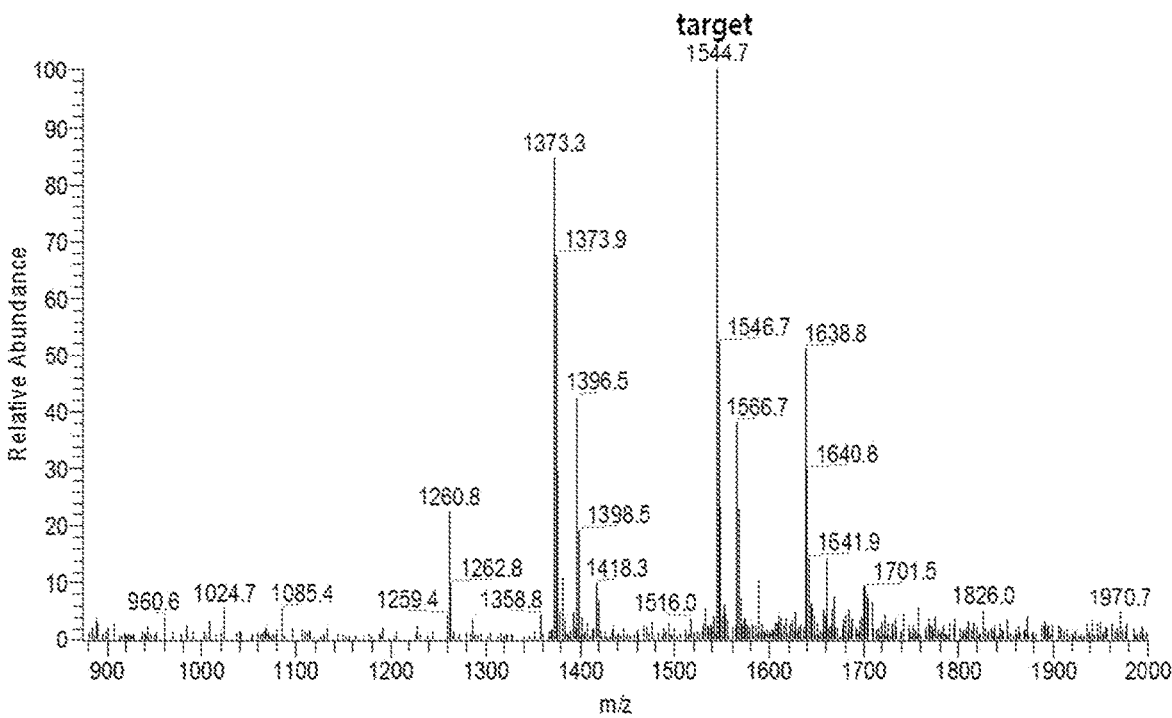

[FIG. 7]
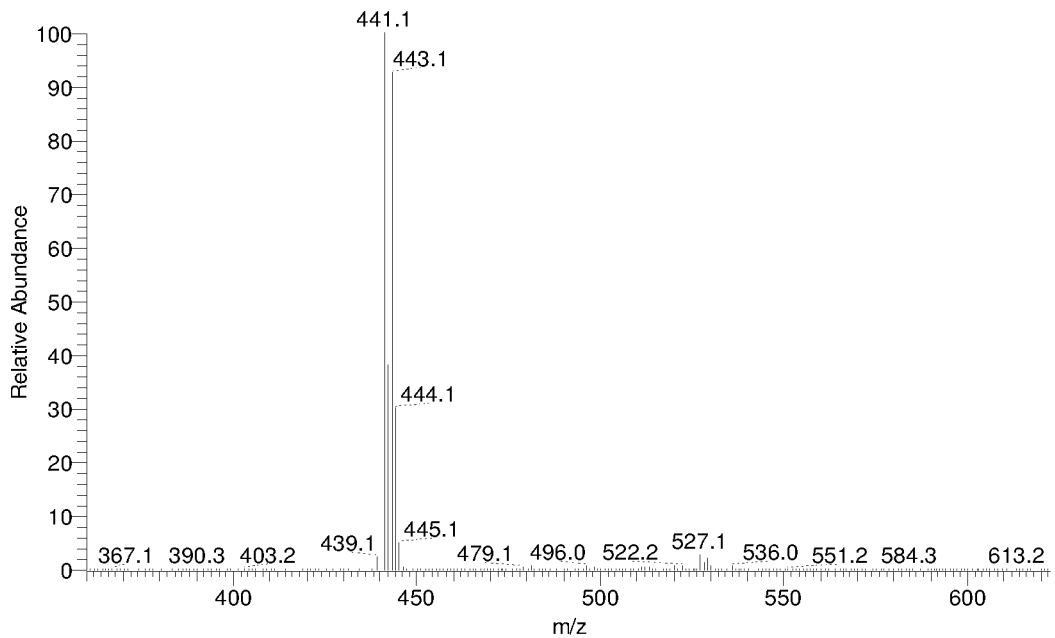
[FIG. 8]
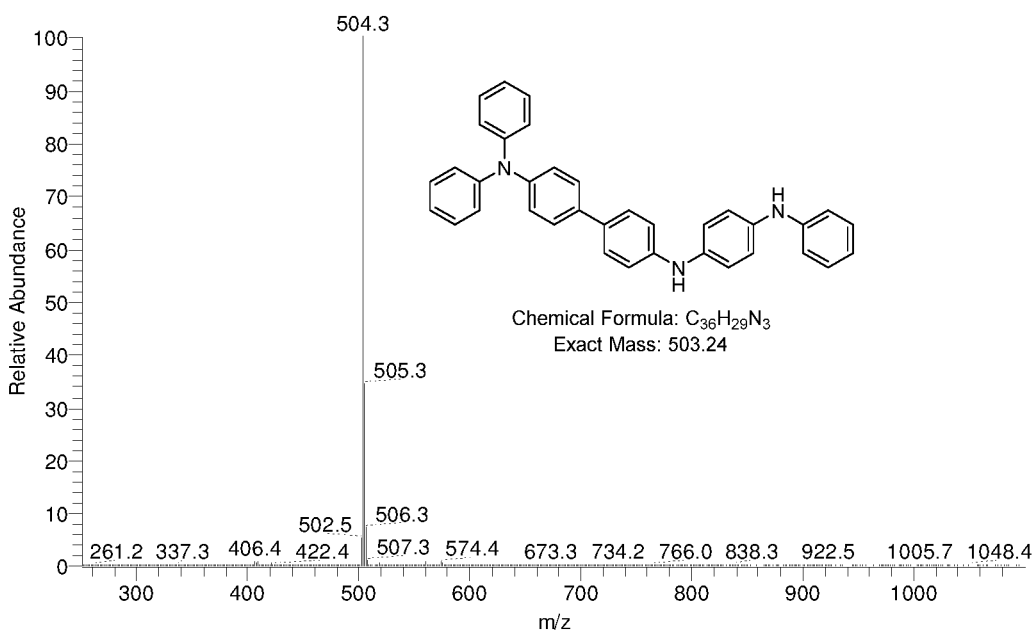

COATING COMPOSITION COMPRISING COMPOUND, AND ORGANIC LIGHT EMITTING DEVICE COMPRISING SAME

CROSS-REFERENCE TO RELATED APPLICATIONS

The present application is a national phase entry under 35 U.S.C. § 371 of International Application No. PCT/KR2018/006286 filed Jun. 1, 2018, which claims priority from Korean Patent Application No. 10-2017-0086663 filed Jul. 7, 2017, all of which are incorporated herein by reference.

TECHNICAL FIELD

The present specification relates to a coating composition comprising a compound, and an organic light emitting device comprising the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic electroluminescent device using such a principle may be generally formed with a cathode, an anode, and an organic material layer placed therebetween, for example, an organic material layer comprising a hole injection layer, a hole transfer layer, a light emitting layer, an electron transfer layer and an electron injection layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. NPB (n-propyl bromide) normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS (poly(3,4-ethylenedioxythiophene) doped with poly(styrenesulfonic acid)) currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

Accordingly, development of organic materials fulfilling such requirements has been required in the art.

PRIOR ART DOCUMENTS

Patent Documents

Korean Patent Application Laid-Open Publication No. 10-2004-0028954

DISCLOSURE

Technical Problem

The present specification relates to a coating composition comprising a compound, and an organic light emitting device comprising the same.

Technical Solution

One embodiment of the present specification provides a coating composition comprising a compound represented by the following Chemical Formula 1 and a compound represented by the following Chemical Formula 2.

[Chemical Formula 1]

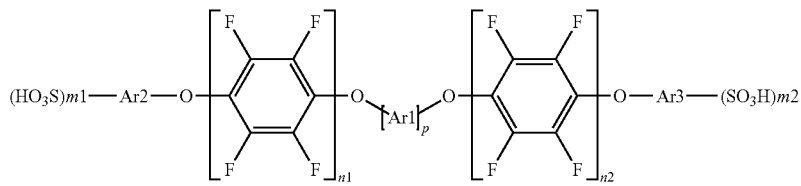

In Chemical Formula 1,

Ar1 is a substituted or unsubstituted alkylene group; a substituted or unsubstituted divalent carbonyl group; a substituted or unsubstituted divalent amine group; or a substituted or unsubstituted arylene group, Ar2 and Ar3 are the same as or different from each other, and each independently a substituted or unsubstituted arylene group, m1, m2, n1 and n2 are the same as or different from each other, and each independently an integer of 1 to 10, when n1 and n2 are each 2 or greater, structures in the parentheses are the same as or different from each other, and p is an integer of 2 to 10 and two or more Ar1s are the same as or different from each other,

[Chemical Formula 2]

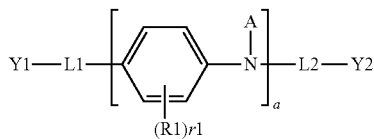

in Chemical Formula 2,

L1 and L2 are the same as or different from each other, and each independently a direct bond; a substituted or unsubstituted arylene group; or a substituted or unsubstituted heteroarylene group, A, R1, Y1 and Y2 are the same as or different from each other, and each independently hydrogen; deuterium; a substituted or unsubstituted alkyl group; a substituted or unsubstituted cycloalkyl group; a substituted or unsubstituted amine group; a substituted or unsubstituted aryl group; or a substituted or unsubstituted heterocyclic group, a is an integer of 1 to 10, when a is 2 or greater, structures in the parentheses are the same as or different from each other, r1 is an integer of 1 to 4, and when r1 is 2 or greater, a plurality of R1s are the same as or different from each other.

Another embodiment of the present specification provides a first electrode; a second electrode provided opposite to the first electrode; and one or more organic material layers provided between the first electrode and the second electrode, wherein one or more layers of the organic material layers comprise the coating composition.

Still another embodiment of the present specification provides a method for manufacturing an organic light emitting device comprising preparing a substrate; forming a first electrode on the substrate; forming one or more organic material layers on the first electrode; and forming a second electrode on the organic material layers, wherein the forming of the organic material layers comprises forming one or more organic material layers using the coating composition.

Advantageous Effects

A coating composition according to one embodiment of the present specification does not have solubility for other solvents, and therefore, a lamination film-forming process can be performed on the formed film through another solution process.

A coating composition according to one embodiment of the present specification can be used as a material of an organic material layer of an organic light emitting device, and is capable of providing long lifetime properties.

DESCRIPTION OF DRAWINGS

FIG. 1 illustrates an example of an organic light emitting device according to one embodiment of the present specification.

FIG. 2 is a diagram showing an NMR spectrum of Compound 1-1.

FIG. 3 is a diagram showing an NMR spectrum of Chemical Formula 1-2.

FIG. 4 is a diagram showing an MS spectrum of Chemical Formula 1-3.

FIG. 5 is a diagram showing an MS spectrum of Chemical Formula 1-4.

FIG. 6 is a diagram showing an MS spectrum of Chemical Formula 1-5.

FIG. 7 is a diagram showing an MS spectrum of Chemical Formula 2-1.

FIG. 8 is a diagram showing an MS spectrum of Chemical Formula 2-2.

MODE FOR DISCLOSURE

Hereinafter, the present specification will be described in more detail.

One embodiment of the present specification provides a coating composition comprising a compound represented by Chemical Formula 1 and a compound represented by Chemical Formula 2.

The compound represented by Chemical Formula 1 of the present specification may perform a role of a dopant in a hole injection layer, and the compound represented by Chemical Formula 2 of the present specification may perform a role of a host in the hole injection layer. Specifically, the compound represented by Chemical Formula 1 of the present specification may perform a role of a dopant of the compound represented by Chemical Formula 2 of the present specification.

In addition, the fluorine-substituted phenyl group of Chemical Formula 1 of the present specification may enhance performance by working with the compound represented by Chemical Formula 2 of the present specification, and the sulfonic acid group of Chemical Formula 1 of the present specification may prevent the compound from being dissolved and migrating during a solution process of an OLED, and therefore, excellent effects are obtained in performance and process.

In the present specification, a description of a certain member being placed "on" another member includes not only a case of the one member adjoining the another member but a case of still another member being present between the two members.

In the present specification, a description of a certain part "comprising" certain constituents means capable of further comprising other constituents, and does not exclude other constituents unless particularly stated on the contrary.

Examples of substituents in the present specification are described below, however, the substituents are not limited thereto.

In the present specification,

means a linking site.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a hydroxyl group; a carbonyl group; an ester group; an alkyl group; a cycloalkyl group; an amine group; an aryl group; and a heterocyclic group including one or more of N, O, S, Se and Si atoms, or being substituted with a substituent linking two or more substituents among the substituents illustrated above, or having no substituents.

In the present specification, examples of the halogen group may include fluorine, chlorine, bromine or iodine.

In the present specification, the number of carbon atoms of the carbonyl group is not particularly limited, but is preferably from 1 to 50. Specifically, compounds having structures as below may be included, however, the carbonyl group is not limited thereto.

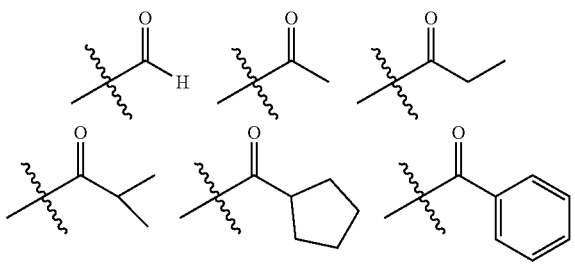

-continued

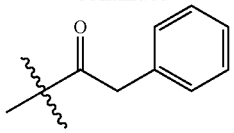

In the present specification, the number of carbon atoms of the ester group is not particularly limited, but is preferably from 1 to 50. Specifically, compounds having the following structural formulae may be included, however, the ester group is not limited thereto.

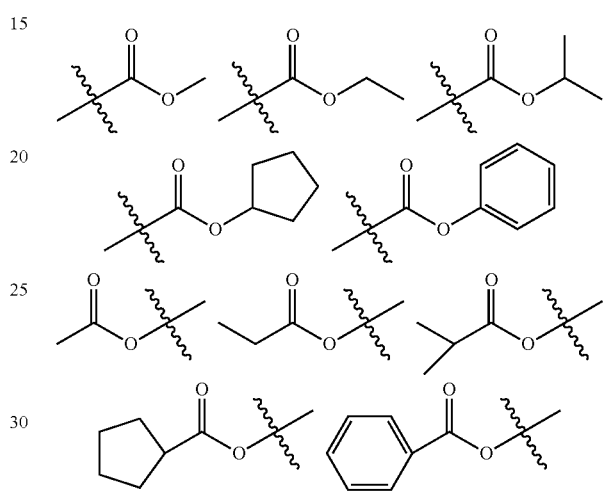

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 60 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, when the aryl group is a monocyclic aryl group, the number of carbon atoms is not particularly limited, but is preferably from 6 to 50. Specific examples of the monocyclic aryl group may include a phenyl group, a biphenyl group, a terphenyl group, a quaterphenyl group and the like, but are not limited thereto.

When the aryl group is a polycyclic aryl group, the number of carbon atoms is not particularly limited, but is preferably from 10 to 50. Specific examples of the polycyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

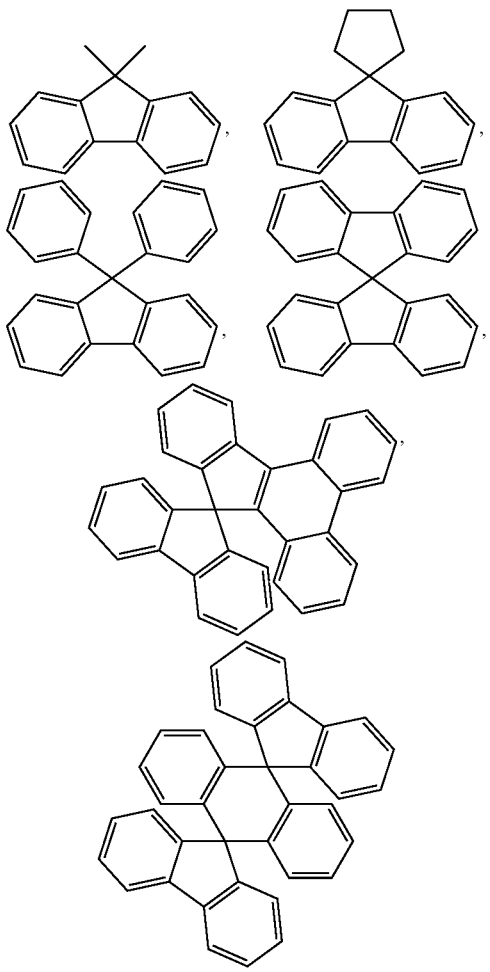

and the like may be included. However, the compound is not limited thereto.

In the present specification, the heterocyclic group includes one or more of N, O, S, Si and Se as a heteroatom, and although not particularly limited thereto, the number of carbon atoms is preferably from 2 to 60. Examples of the heterocyclic group may include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a dibenzofuranyl group and the like, but are not limited thereto.

In the present specification, the heteroaryl group may be selected from among the examples of the heterocyclic group except for those that are aromatic.

In the present specification, the amine group is represented by —NR$_a$R$_b$, R$_a$ and R$_b$ are the same as or different from each other, and may be each independently a substituent formed with at least one of hydrogen, deuterium, a halogen group, an alkyl group, an alkenyl group, an alkoxy group, a cycloalkyl group, an aryl group and a heterocyclic group. For example, the amine group may be selected from the group consisting of —NH$_2$, a monoalkylamine group, a dialkylamine group, an N-alkylarylamine group, a monoarylamine group, a diarylamine group, an N-arylheteroarylamine group, an N-alkylheteroarylamine group, a monoheteroarylamine group and a diheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups. For example, the aryl group in the arylamine group may be selected from among the examples of the aryl group described above.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, polycyclic heteroaryl groups, or both monocyclic heteroaryl groups and polycyclic heteroaryl groups. For example, the heteroaryl group in the heteroarylamine group may be selected from among the examples of the heteroaryl group described above.

In the present specification, an aromatic cyclic group may be monocyclic or polycyclic, and may be selected from among the examples of the aryl group except for those that are not monovalent.

In the present specification, the divalent to tetravalent aromatic cyclic group may be monocyclic or polycyclic, and means having the aryl group having 2 to 4 bonding sites, that is, a divalent to tetravalent group. Descriptions on the aryl group provided above may be applied thereto except for each being a divalent to tetravalent group.

In the present specification, the alkylene group means the alkyl group having two bonding sites, that is, a divalent group. Descriptions on the alkyl group provided above may be applied thereto except for each being a divalent group.

In the present specification, the arylene group means the aryl group having two bonding sites, that is, a divalent group. Descriptions on the aryl group provided above may be applied thereto except for each being a divalent group.

In the present specification, the heteroarylene group means the heteroaryl group having two bonding sites, that is, a divalent group. Descriptions on the heteroaryl group provided above may be applied thereto except for each being a divalent group.

In one embodiment of the present specification, An is a substituted or unsubstituted alkylene group; a substituted or unsubstituted divalent carbonyl group; a substituted or unsubstituted divalent amine group; or a substituted or unsubstituted arylene group.

In one embodiment of the present specification, An is a substituted or unsubstituted alkylene group having 1 to 20 carbon atoms.

In one embodiment of the present specification, An is an alkylene group unsubstituted or substituted with hydrogen, deuterium, a halogen group, a nitrile group, an alkyl group, a cycloalkyl group, an amine group, an aryl group or a heterocyclic group.

In one embodiment of the present specification, An is an alkylene group unsubstituted or substituted with a trifluoroalkyl group.

In one embodiment of the present specification, An is a substituted or unsubstituted divalent carbonyl group having 1 to 20 carbon atoms.

In one embodiment of the present specification, An is a divalent carbonyl group unsubstituted or substituted with hydrogen, deuterium, a halogen group, a nitrile group, an alkyl group, a cycloalkyl group, an amine group, an aryl group or a heterocyclic group.

In one embodiment of the present specification, An is a divalent carbonyl group.

In one embodiment of the present specification, An is a substituted or unsubstituted divalent amine group having 1 to 50 carbon atoms.

In one embodiment of the present specification, An is a divalent amine group unsubstituted or substituted with hydrogen, deuterium, a halogen group, a nitrile group, an alkyl group, a cycloalkyl group, an amine group, an aryl group or a heterocyclic group.

In one embodiment of the present specification, An is a divalent amine group unsubstituted or substituted with an aryl group.

In one embodiment of the present specification, An is a divalent amine group unsubstituted or substituted with a phenyl group.

In one embodiment of the present specification, An is a substituted or unsubstituted arylene group having 6 to 50 carbon atoms.

In one embodiment of the present specification, An is an arylene group unsubstituted or substituted with hydrogen, deuterium, a halogen group, a nitrile group, an alkyl group, a cycloalkyl group, an amine group, an aryl group or a heterocyclic group.

In one embodiment of the present specification, An is a phenylene group unsubstituted or substituted with hydrogen, deuterium, a halogen group, a nitrile group, an alkyl group, a cycloalkyl group, an amine group, an aryl group or a heterocyclic group.

In one embodiment of the present specification, An is a phenylene group.

In one embodiment of the present specification, An is a divalent fluorenyl group unsubstituted or substituted with hydrogen, deuterium, a halogen group, a nitrile group, an alkyl group, a cycloalkyl group, an amine group, an aryl group or a heterocyclic group.

In one embodiment of the present specification, An is a divalent fluorenyl group.

In one embodiment of the present specification, An may be selected from among the following A-1 to A-5.

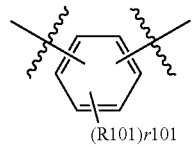

A-1

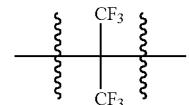

A-2

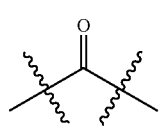

A-3

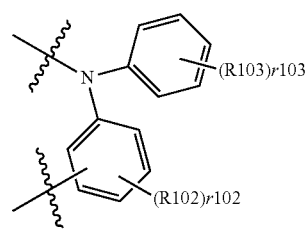

A-4

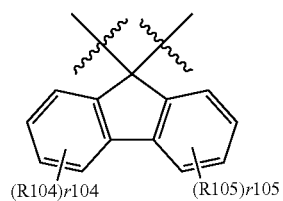

A-5

In one embodiment of the present specification, R101 to R105 are the same as or different from each other, and each independently hydrogen; deuterium; a halogen group; a nitrile group; a substituted or unsubstituted alkyl group; a substituted or unsubstituted cycloalkyl group; a substituted or unsubstituted amine group; a substituted or unsubstituted aryl group; or a substituted or unsubstituted heterocyclic group.

In one embodiment of the present specification, r101, r102, r104 and r105 are each an integer of 1 to 4, r103 is an integer of 1 to 5, and when r101 to r105 are each 2 or greater, two or more R101s to R105s are the same as or different from each other.

In one embodiment of the present specification, R101 to R105 are each hydrogen.

In one embodiment of the present specification, Ar2 and Ar3 are the same as or different from each other, and each independently a substituted or unsubstituted arylene group.

In one embodiment of the present specification, Ar2 is a substituted or unsubstituted arylene group having 6 to 50 carbon atoms.

In one embodiment of the present specification, Ar2 is a substituted or unsubstituted naphthylene group.

In one embodiment of the present specification, Ar2 is a naphthylene group.

In one embodiment of the present specification, Ar3 is a substituted or unsubstituted arylene group having 6 to 50 carbon atoms.

In one embodiment of the present specification, Ar3 is a substituted or unsubstituted naphthylene group.

In one embodiment of the present specification, Ar3 is a naphthylene group.

In one embodiment of the present specification, m1, m2, n1 and n2 are the same as or different from each other, and each independently an integer of 1 to 10, and when n1 and n2 are each 2 or greater, structures in the parentheses are the same as or different from each other.

In one embodiment of the present specification, m1 is an integer of 1 to 5.

In one embodiment of the present specification, m1 is 2.

In one embodiment of the present specification, m2 is an integer of 1 to 5.

In one embodiment of the present specification, m2 is 2.

In one embodiment of the present specification, n1 is an integer of 1 to 5.

In one embodiment of the present specification, n1 is 2.

In one embodiment of the present specification, n2 is an integer of 1 to 5.

In one embodiment of the present specification, n2 is 2.

In one embodiment of the present specification, p is an integer of 2 to 10, and two or more Ar1s are the same as or different from each other.

In one embodiment of the present specification, p is an integer of 2 to 5.

In one embodiment of the present specification, p is 3.

In one embodiment of the present specification, p is 5.

In one embodiment of the present specification, —[Ar1]p— may be selected from among the following A-11 to A-15.

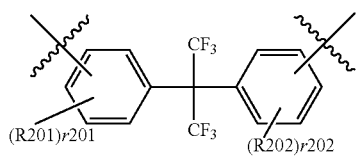

A-11

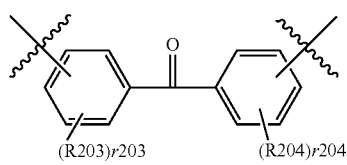

A-12

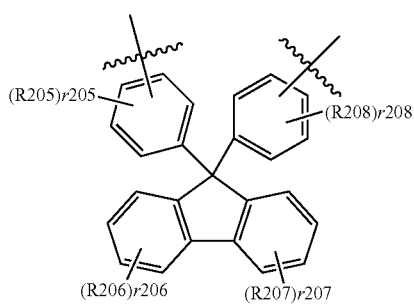

A-13

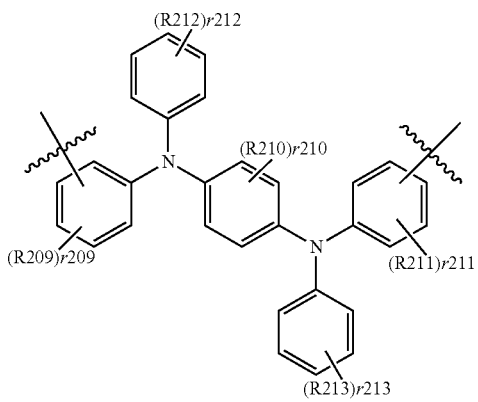

A-14

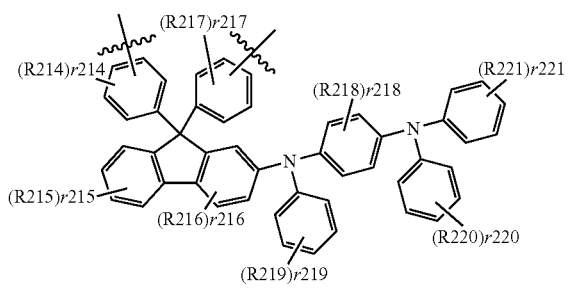

A-15

In one embodiment of the present specification, A-11 may be formed by A-2 and two A-1s bonding to each other, and p is 3.

In one embodiment of the present specification, A-12 may be formed by A-3 and two A-1s bonding to each other, and p is 3.

In one embodiment of the present specification, A-13 may be formed by A-5 and two A-1s bonding to each other, and p is 3.

In one embodiment of the present specification, A-14 may be formed by A-1 and two A-4s bonding to each other, and p is 3.

In one embodiment of the present specification, A-15 may be formed by A-5, two A-1s and two A-4s bonding to each other, and p is 5.

In one embodiment of the present specification, R201 to R221 are the same as or different from each other, and each independently hydrogen; deuterium; a halogen group; a nitrile group; a substituted or unsubstituted alkyl group; a substituted or unsubstituted cycloalkyl group; a substituted or unsubstituted amine group; a substituted or unsubstituted aryl group; or a substituted or unsubstituted heterocyclic group.

In one embodiment of the present specification, r201 to r211, r214, r215, r217 and r218 are each an integer of 1 to 4, r212, r213 and r219 to r221 are each an integer of 1 to 5, r216 is an integer of 1 to 3, and when r201 to r221 are each 2 or greater, two or more R201s to R221s are the same as or different from each other.

In one embodiment of the present specification, R201 to R221 are each hydrogen.

In one embodiment of the present specification, L1 and L2 are the same as or different from each other, and each independently a direct bond; a substituted or unsubstituted arylene group; or a substituted or unsubstituted heteroarylene group.

In one embodiment of the present specification, L1 is a direct bond.

In one embodiment of the present specification, L1 is a substituted or unsubstituted arylene group having 6 to 30 carbon atoms.

In one embodiment of the present specification, L1 is a substituted or unsubstituted phenylene group, a substituted or unsubstituted biphenylene group, or a substituted or unsubstituted naphthylene group.

In one embodiment of the present specification, L1 is a phenylene group.

In one embodiment of the present specification, L1 is a biphenylene group.

In one embodiment of the present specification, L1 is a naphthylene group.

In one embodiment of the present specification, L2 is a direct bond.

In one embodiment of the present specification, L2 is a substituted or unsubstituted arylene group having 6 to 30 carbon atoms.

In one embodiment of the present specification, L2 is a substituted or unsubstituted phenylene group, a substituted or unsubstituted biphenylene group, or a substituted or unsubstituted naphthylene group.

In one embodiment of the present specification, L2 is a phenylene group.

In one embodiment of the present specification, L2 is a biphenylene group.

In one embodiment of the present specification, L2 is a naphthylene group.

In one embodiment of the present specification, A, R1, Y1 and Y2 are the same as or different from each other, and each independently hydrogen; deuterium; a substituted or unsubstituted alkyl group; a substituted or unsubstituted cycloalkyl group; a substituted or unsubstituted amine group; a substituted or unsubstituted aryl group; or a substituted or unsubstituted heterocyclic group.

In one embodiment of the present specification, a is an integer of 1 to 10, and when a is 2 or greater, structures in the parentheses are the same as or different from each other, and r1 is an integer of 1 to 4, and when r1 is 2 or greater, a plurality of R1s are the same as or different from each other.

In one embodiment of the present specification, A is hydrogen.

In one embodiment of the present specification, R1 is hydrogen.

In one embodiment of the present specification, Y1 is hydrogen.

In one embodiment of the present specification, Y1 is a substituted or unsubstituted amine group having 1 to 50 carbon atoms.

In one embodiment of the present specification, Y1 is an amine group unsubstituted or substituted with an aryl group.

In one embodiment of the present specification, Y1 is an amine group unsubstituted or substituted with a phenyl group.

In one embodiment of the present specification, Y2 is hydrogen.

In one embodiment of the present specification, Y2 is a substituted or unsubstituted aryl group having 6 to 50 carbon atoms.

In one embodiment of the present specification, Y2 is a substituted or unsubstituted phenyl group.

In one embodiment of the present specification, Y2 is a phenyl group.

In one embodiment of the present specification, $(m1+m2)/(n1+n2) \leq 1$.

When laminating a hole injection layer and a hole transfer layer in a solution process, the sulfonic group of Chemical Formula 1 of the present specification is able to prevent the hole injection layer material from moving to the hole transfer layer using solvent resistance, and therefore, having m1, m2, n1 and n2 representing electrical properties in the above-mentioned range is very effective in device performance and long lifetime.

In one embodiment of the present specification, the compound represented by Chemical Formula 1 is any one selected from among the following Chemical Formula 1-1 to Chemical Formula 1-5.

[Chemical Formula 1-1]

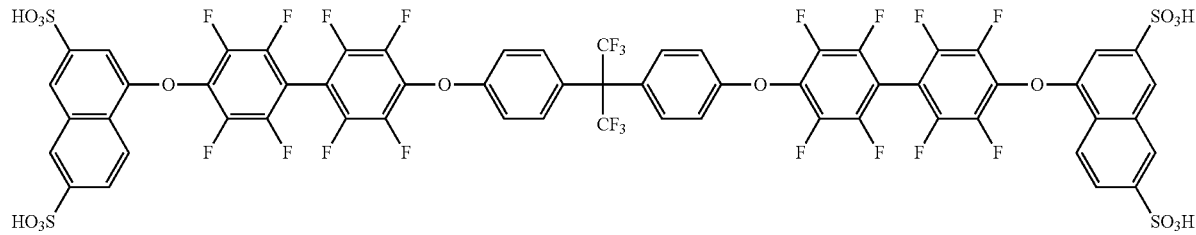

[Chemical Formula 1-2]

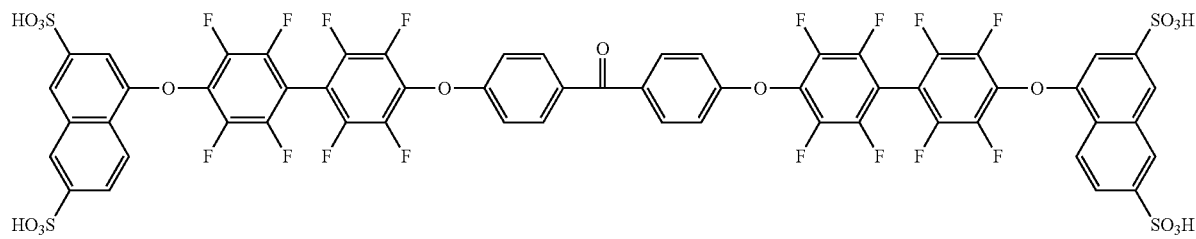

[Chemical Formula 1-3]
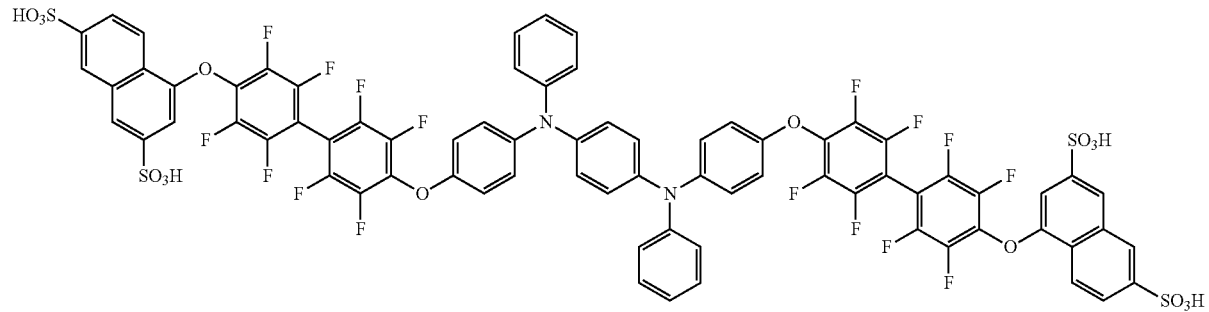
[Chemical Formula 1-4]
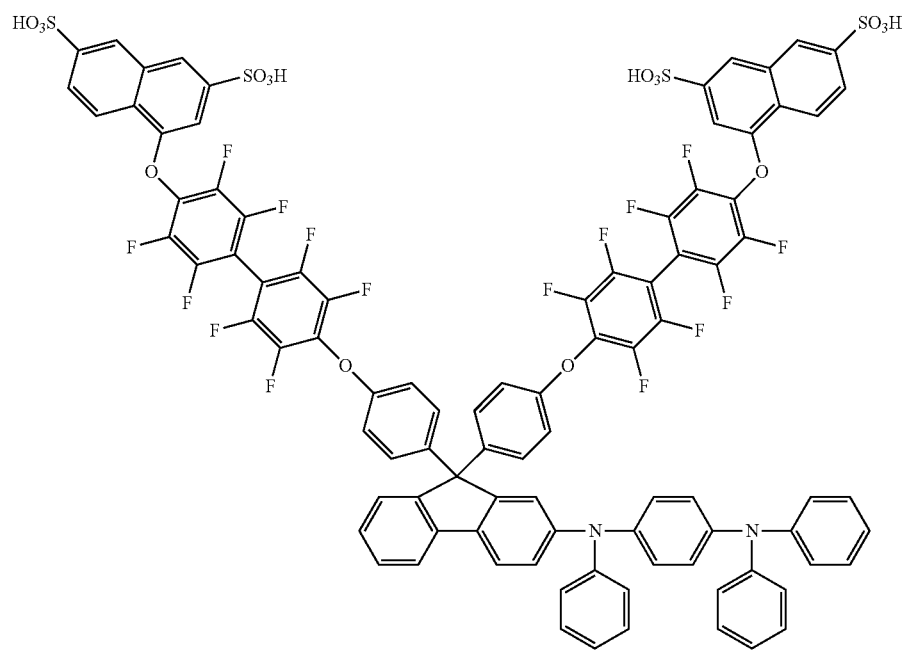

[Chemical Formula 1-5]

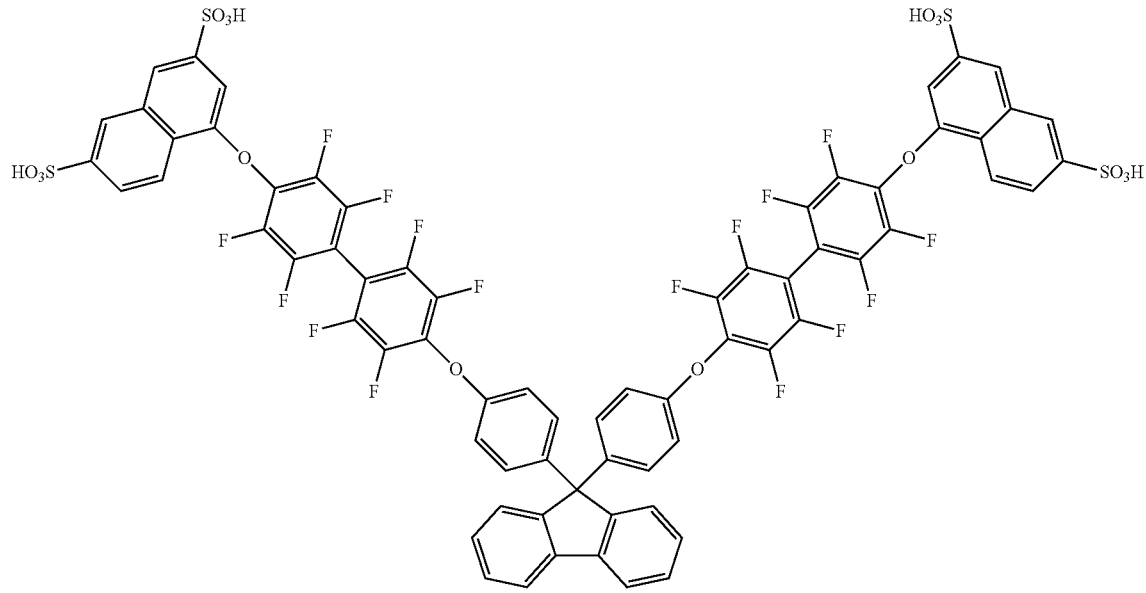

According to one embodiment of the present specification, the compound represented by Chemical Formula 2 is the following Chemical Formula 2-1 or 2-2.

[Chemical Formula 2-1]

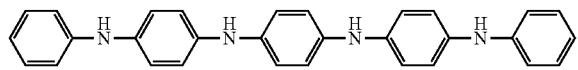

[Chemical Formula 2-2]

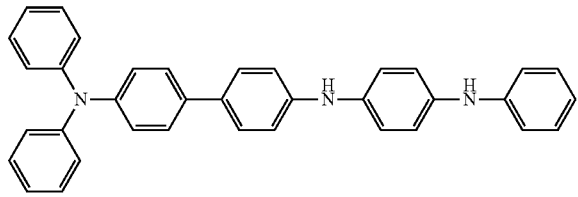

In one embodiment of the present specification, the coating composition may further comprise a solvent.

In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone or cyclohexanone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; benzoate-based solvents such as methyl benzoate, butyl benzoate or 3-phenoxybenzoate; tetraline, and the like, however, the solvent is not limited thereto as long as it is a solvent capable of dissolving or dispersing the compound according to one embodiment of the present disclosure.

In another embodiment, the solvent may be used either alone as one type, or as a mixture mixing two or more solvent types.

In another embodiment, the solvent has a boiling point of preferably 40° C. to 250° C. and more preferably 60° C. to 230° C., however, the boiling point is not limited thereto.

In another embodiment, the single or mixed solvent has viscosity of preferably 1 cP to 10 cP and more preferably 3 CP to 8 CP, however, the viscosity is not limited thereto.

In another embodiment, the coating composition has a concentration of preferably 0.1 wt/v % to 20 wt/v % and more preferably 0.5 wt/v % to 5 wt/v %, however, the concentration is not limited thereto.

In one embodiment of the present specification, the coating composition may further comprise one, two or more types of additives selected from the group consisting of thermal polymerization initiators and photopolymerization initiators.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5, 5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like. In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

Another embodiment of the present specification provides an organic light emitting device formed by using the coating composition.

In one embodiment of the present specification, the organic light emitting device comprises a first electrode; a second electrode; and one or more organic material layers provided between the first electrode and the second electrode, wherein one or more layers of the organic material layers are formed by using the coating composition.

In one embodiment of the present specification, the first electrode is a cathode, and the second electrode is an anode.

In another embodiment, the first electrode is an anode, and the second electrode is a cathode.

In one embodiment of the present specification, the organic material layer formed by using coating composition is a hole transfer layer, a hole injection layer, or a layer carrying out hole transfer and hole injection at the same time.

In one embodiment of the present specification, the organic light emitting device further comprises one, two or more layers selected from the group consisting of a hole injection layer, a hole transfer layer, an electron transfer layer, an electron injection layer, an electron blocking layer and a hole blocking layer.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

In one embodiment of the present specification, the hole injection layer (301), the hole transfer layer (401) or the light emitting layer (501) of FIG. 1 may be formed by using the coating composition comprising the compound represented by Chemical Formula 1.

In one embodiment of the present specification, the hole injection layer (301) of FIG. 1 may be formed by using the coating composition comprising the compound represented by Chemical Formula 1.

In one embodiment of the present specification, the hole transfer layer (401) of FIG. 1 may be formed by using the coating composition comprising the compound represented by Chemical Formula 1.

FIG. 1 illustrates the organic light emitting device, however, the organic light emitting device is not limited thereto.

When the organic light emitting device comprises a plurality of organic material layers, the organic material layers may be formed with materials that are the same as or different from each other.

The organic light emitting device of the present specification may be manufactured using materials and methods known in the art, except that one or more layers of the organic material layers are formed by using the coating composition.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, one embodiment of the present specification also provides a method for manufacturing an organic light emitting device formed using the coating composition.

Specifically, the method for manufacturing an organic light emitting device in one embodiment of the present specification comprises preparing a substrate; forming a cathode or an anode on the substrate; forming one or more organic material layers on the cathode or the anode; and forming an anode or a cathode on the organic material layers, wherein one or more layers of the organic material layers are formed by using the coating composition.

In one embodiment of the present specification, the organic material layer formed by using the coating composition is formed by using spin coating.

In another embodiment, the organic material layer formed by using the coating composition is formed by using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed by using a printing method, and therefore, is economically effective in terms of time and costs when manufacturing a device.

In one embodiment of the present specification, the forming of an organic material layer formed by using the coating composition comprises coating the coating composition on the cathode or the anode; and heat treating or light treating the coated coating composition.

In one embodiment of the present specification, the time of heat treating the organic material layer formed by using the coating composition is preferably within 1 hour and more preferably within 30 minutes.

In one embodiment of the present specification, the atmosphere of heat treating the organic material layer formed by using the coating composition is preferably inert gas such as argon or nitrogen.

When the heat treatment or the light treatment is comprised in the forming of an organic material layer formed by using the coating composition, an organic material layer comprising a thin-filmed structure by a plurality of the compound of Chemical Formula 1 comprised in the coating composition forming crosslinkage may be provided. In this case, the organic material layer formed by using the coating composition may be prevented from being dissolved by a solvent deposited on the surface, or being morphologically affected or decomposed.

Accordingly, when the organic material layer formed by using the coating composition is formed comprising the heat treatment or the light treatment, resistance for the solvent increases, and multiple layers may be formed by repeatedly carrying out solution deposition and crosslinking methods, and as a result, lifetime properties of a device may be enhanced by increasing stability.

In one embodiment of the present specification, the coating composition comprising the compound may use a coating composition mixed and dispersed to a polymer binder.

As the polymer binder in one embodiment of the present specification, those that do not extremely inhibit charge transfer are preferred, and those that do not exhibit strong absorption for visible light are preferably used. Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, the compound according to one embodiment of the present specification may be comprised alone in the organic material layer, may be thin-filmed through heat treating or light treating a coating composition comprising the compound, or may be comprised as a copolymer using a coating composition mixed with other monomers. In addition, a copolymer or a mixture may be comprised using a coating composition mixed with other polymers.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2/Al$, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, or the like, but are not limited thereto.

The light emitting layer may comprise a host material and a dopant material.

The host material of the light emitting layer includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material of the light emitting layer includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, aluminum complexes and the like are included, however, the material is not limited thereto.

The organic light emitting device according to the present specification may be a top-emission type, a bottom-emission type or a dual-emission type depending on the materials used.

In one embodiment of the present specification, the coating composition may be comprised in organic solar cells or organic transistors in addition to organic light emitting devices.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example

<Preparation Example 1-1>—Preparation of Chemical Formula 1-1

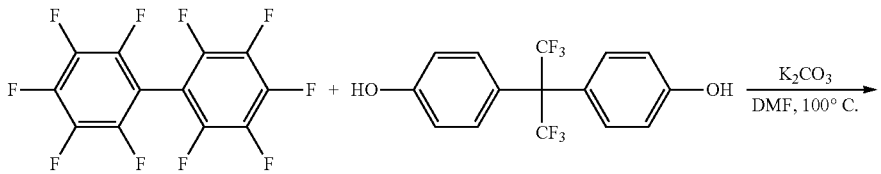

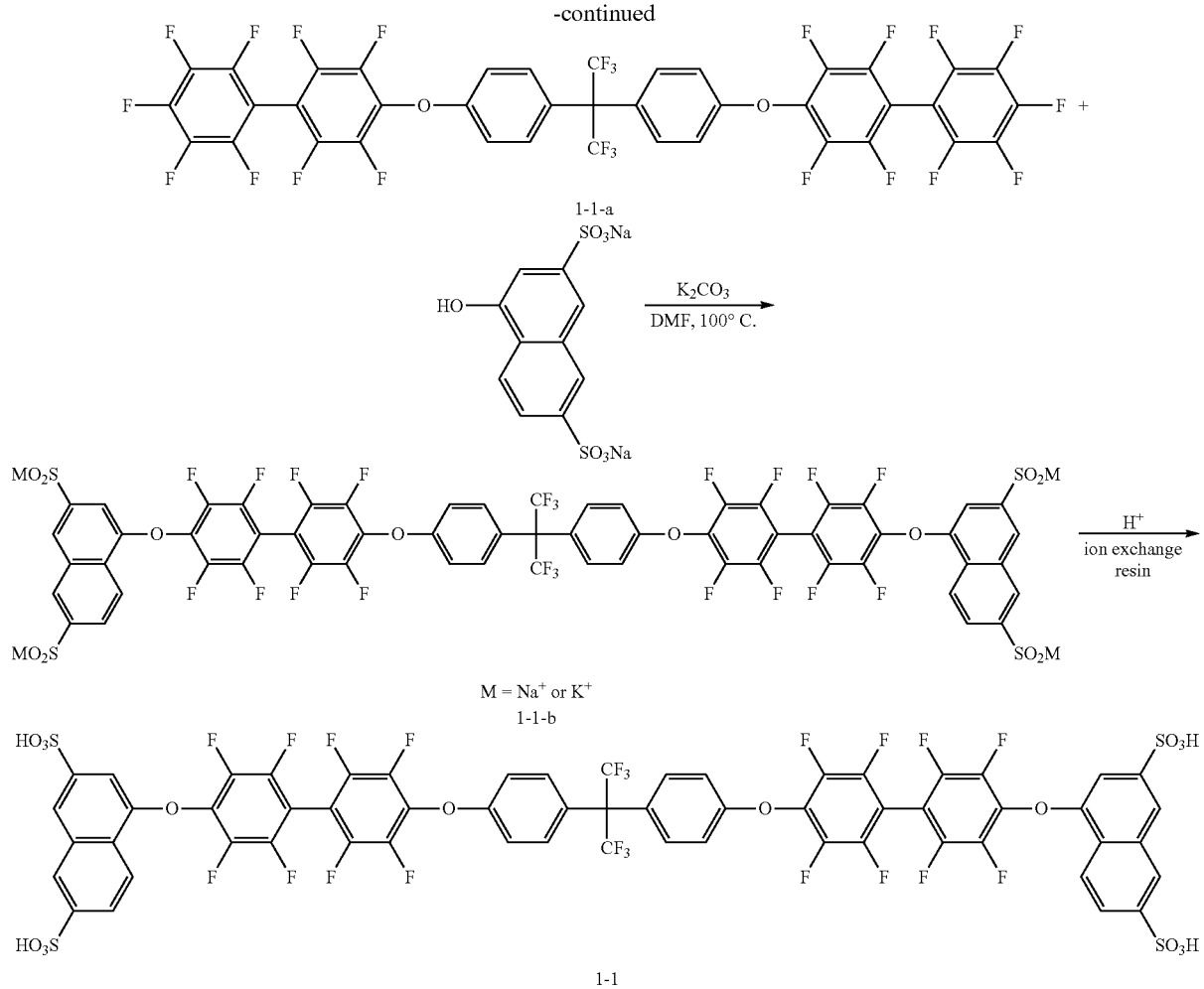

(1) Preparation of Chemical Formula 1-1-a

To 4,4'-(perfluoropropane-2,2-diyl)diphenol (1 g), decafluorodiphenyl (9.94 g), potassium carbonate (0.82 g) and dimethylformamide (DMF) (30 ml) were introduced under nitrogen atmosphere, and after replacing the inside of the reaction vessel with nitrogen, the result was mixed while rotating for 6 hours after adjusting the inner temperature to 100° C. After lowering the temperature to room temperature, N,N-dimethylformamide (150 ml) was introduced thereto to re-dissolve the precipitated compound, and then the result was mixed while rotating for 90 minutes at room temperature. After terminating the mixing, the solution was filtered to remove potassium carbonate residue, and the result was vacuum concentrated. After that, the result was purified through column chromatography to remove remaining impurities, and the remaining decafluorobiphenyl was collected to prepare Chemical Formula 1-1-a.

(2) Preparation of Chemical Formula 1-1-b

To disodium-1-naphthol-3,6,-disulfonate hydrate (1.91 g), Chemical Formula 1-1-a (2.4 g), potassium carbonate (0.72 g) and DMF (25 ml) were introduced under nitrogen atmosphere, and after replacing the inside of the reaction vessel with nitrogen, the result was mixed while rotating for 6 hours after adjusting the inner temperature to 100° C. After lowering the temperature to room temperature, DMF (125 ml) was added thereto to re-dissolve the precipitated compound, and then the result was mixed while rotating for 90 minutes at room temperature. After the mixing, the solution was filtered to remove carbonate residue, and the solution was vacuum concentrated. After adding methanol (90 ml) thereto to remove remaining impurities, the result was mixed while rotating for 30 minutes or longer at room temperature, and then the suspension was filtered and the filtrate was taken. Herein, remaining impurities were separated in a precipitate form by adding methanol (90 ml) thereto, and this was filtered to remove impurities. This process was repeated two or more times for purification until the solution did not become turbid due to impurities when dissolved in methanol. After that, the result was dried in a vacuum oven to prepare Chemical Formula 1-1-b.

(3) Preparation of Chemical Formula 1-1

Ultrapure water (30 ml) was added to Chemical Formula 1-1-b (1 g) for dissolution, and the result was ion exchanged through column chromatography using a cation exchange resin DOWEX Monosphere™ 650 C. After that, a portion with a pH of 1 or less was concentrated and dried under a vacuum condition. After the concentration, the solvent was removed, methylene chloride was added thereto, and the result was stirred for 24 hours to be powdered in a solvent, and then filtered. The powder on a filter paper was dried again in a vacuum oven to obtain Compound 1-1.

FIG. 2 is a diagram showing an NMR spectrum of Compound 1-1.

<Preparation Example 1-2>—Preparation of Chemical Formula 1-2

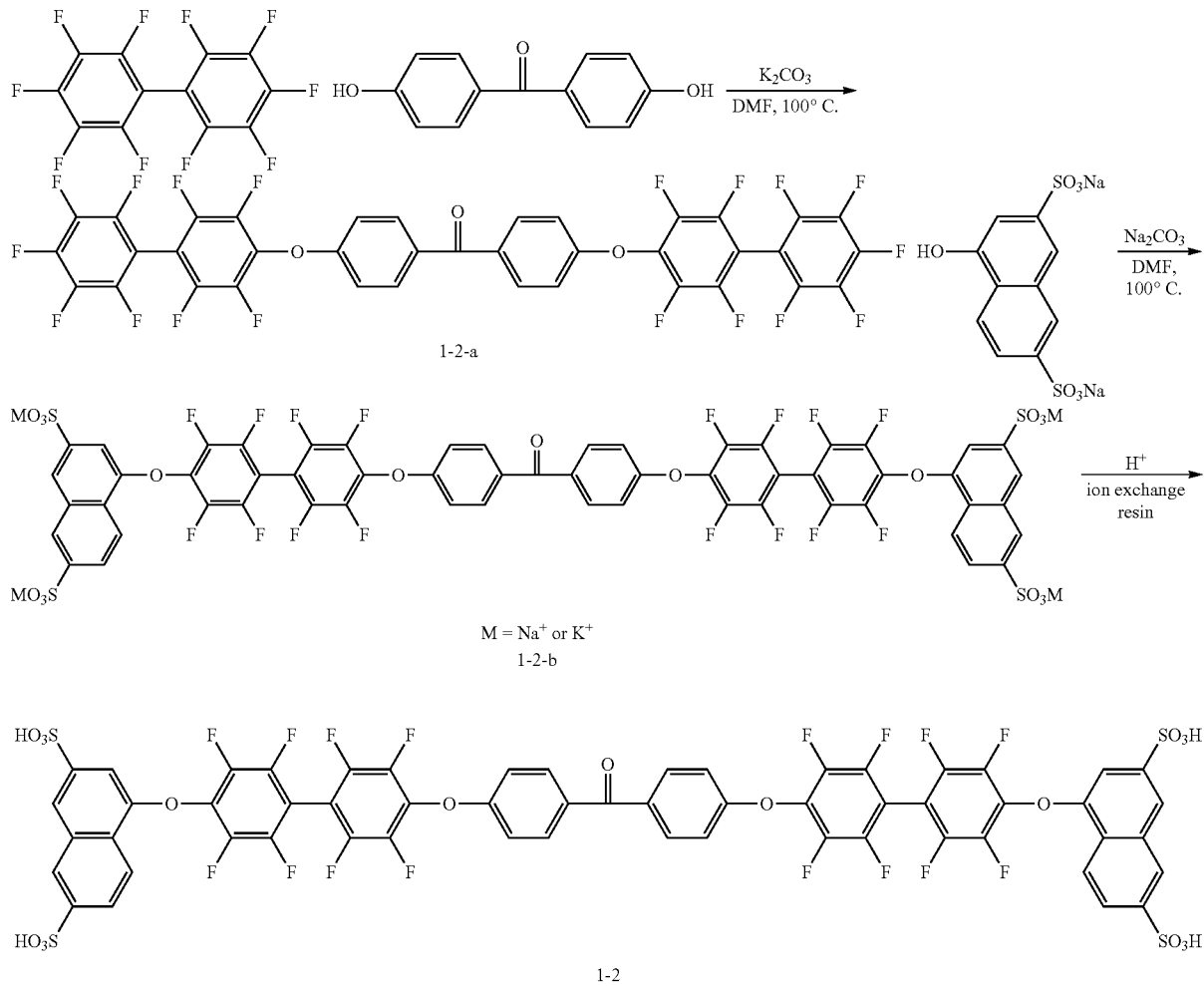

1-2

(1) Preparation of Chemical Formula 1-2-a

To 4,4'-dihydrobenzophenone (1.2 g), decafluorobiphenyl (15.0 g), potassium carbonate (1.55 g) and DMF (56 ml) were added in consecutive order under nitrogen atmosphere, and after replacing the reaction system with nitrogen, the result was stirred while rotating for 6 hours at a solution temperature of 100° C. After lowering the temperature to room temperature by leaving the result unattended, N,N-dimethylformamide (150 ml) was added thereto to re-dissolve the precipitated compound, and then the result was mixed while rotating for 90 minutes at room temperature. After terminating the mixing, the solution was filtered to remove potassium carbonate residue, and the result was vacuum concentrated. Ethanol (100 ml) was added to the concentrated compound, the result was heated to 50° C. or higher to dissolve all the remaining decafluorobiphenyl and passed through a hot-filter. The filtrate was purified and collected after removing the solvent with the remaining decafluorobiphenyl, and solids on the filter paper went through final purification through column chromatography to prepare Chemical Formula 1-2-a.

(2) Preparation of Chemical Formula 1-2-b

To disodium-1-naphthol-3,6-disulfonate hydrate (1.91 g), Chemical Formula 1-2-a (2.4 g), potassium carbonate (0.72 g) and DMF (25 ml) were introduced under nitrogen atmosphere, and after replacing the inside of the reaction vessel with nitrogen, the result was mixed while rotating for 6 hours after adjusting the inner temperature to 100° C. After lowering the temperature to room temperature, DMF (125 ml) was added thereto to re-dissolve the precipitated compound, and then the result was mixed while rotating for 90 minutes at room temperature. After the mixing, the solution was filtered to remove potassium carbonate residue, and the solution was vacuum concentrated. After adding methanol (90 ml) thereto to remove remaining impurities, the result was mixed while rotating for 30 minutes or longer at room temperature, and then the suspension was filtered and the filtrate was taken. Herein, remaining impurities were separated in a precipitate form by adding methanol (90 ml) thereto, and this was filtered to remove impurities. This process was repeated two times or more for purification until the solution did not become turbid due to impurities when dissolved in methanol. After that, the result was dried in a vacuum oven to prepare Chemical Formula 1-2-b.

(3) Preparation of Chemical Formula 1-2

Ultrapure water (30 ml) was added to Chemical Formula 1-2-b (1 g) for dissolution, and the result was ion exchanged through column chromatography using a cation exchange resin DOWEX Monosphere™ 650 C. After that, a portion with a pH of 1 or less was concentrated and dried under a vacuum condition. After the concentration, the solvent was removed, methylene chloride was introduced thereto, and the result was stirred for 24 hours to be powdered in a solvent, then filtered, and the powder on a filter paper was dried again in a vacuum oven to obtain Chemical Formula 1-2.

FIG. 3 is a diagram showing an NMR spectrum of Chemical Formula 1-2.

<Preparation Example 1-3>—Preparation of Chemical Formula 1-3

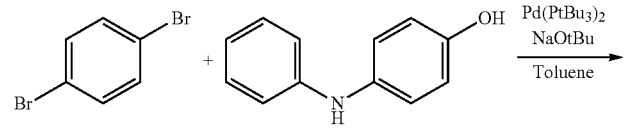

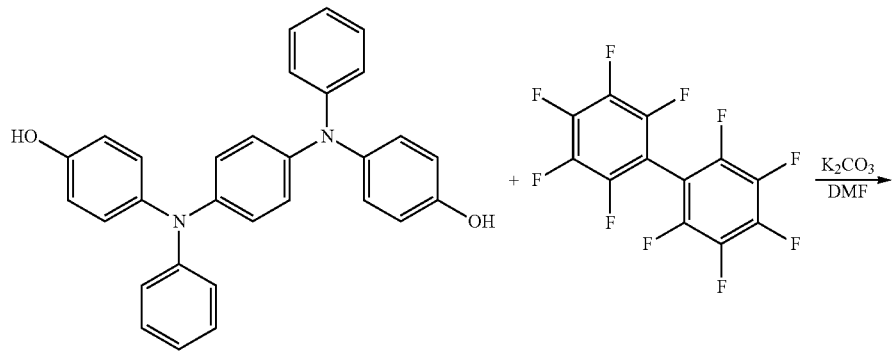

1-3-a

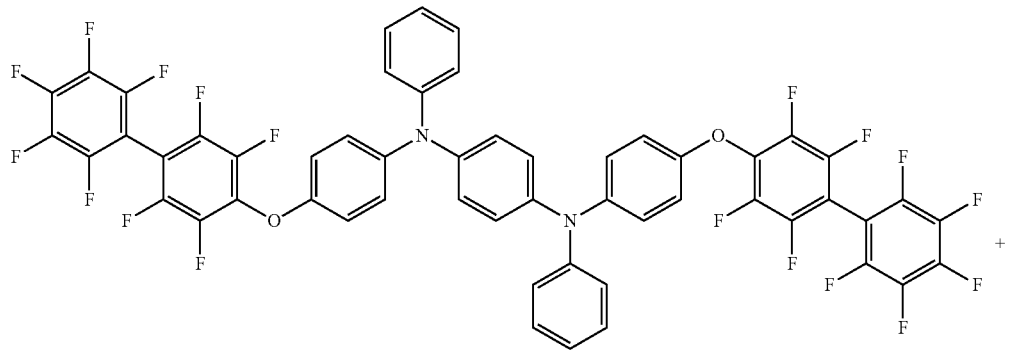

1-3-b

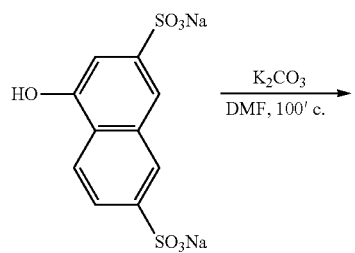

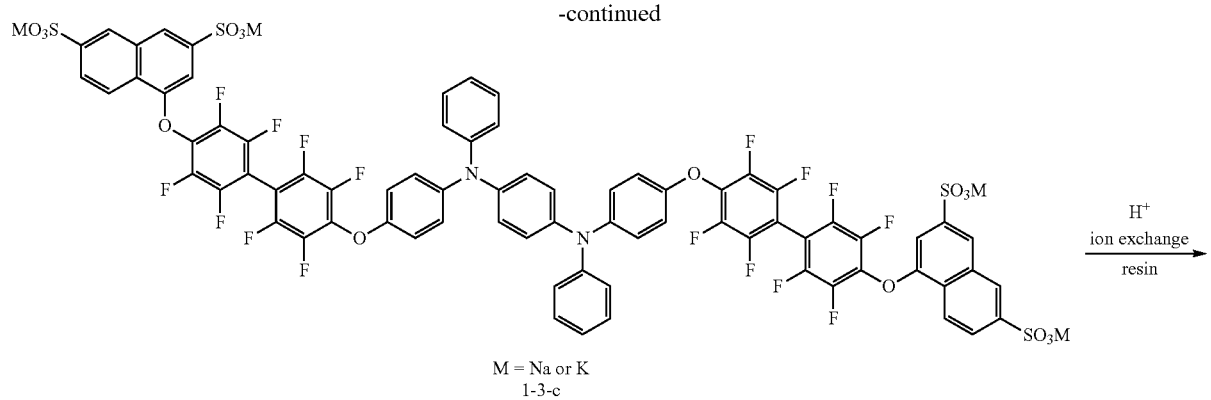

M = Na or K
1-3-c

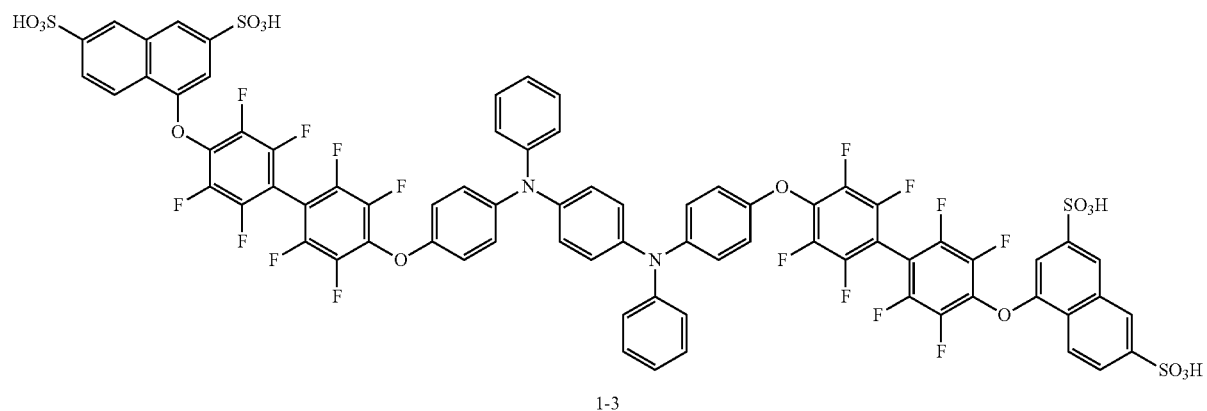 [SMILES: O=S(=O)(O)c1ccc2c(Oc3c(F)c(F)c(-c4c(F)c(F)c(Oc5ccc(N(c6ccccc6)c6ccc(N(c7ccccc7)c7ccc(Oc8c(F)c(F)c(-c9c(F)c(F)c(Oc%10cc(S(=O)(=O)O)cc%11cc(S(=O)(=O)O)ccc%10%11)c(F)c9F)c(F)c8F)cc7)cc6)cc5)c(F)c4F)c(F)c3F)cc(S(=O)(=O)O)cc2c1]

1-3

(1) Preparation of Chemical Formula 1-3-a

To 1,4-dibromobenzene (10 g, 42.4 mmol), 4-(phenylamino)phenol (16.5 g, 89.02 mmol) and sodium-tert-butoxide (NaOtBu, 12.2 g, 127.2 mmol), degassed toluene (150 ml) was introduced for dissolution. After raising the temperature to 100° C., bis(tri-tert-butylphosphine)palladium (0.866 g, 1.69 mmol) was introduced thereto, and the result was reacted for approximately 18 hours. After lowering the temperature to room temperature, water was introduced thereto, and the organic layer was extracted using ethyl acetate. The result was dried with magnesium sulfate ($MgSO_4$), and after adsorbing palladium, the result was filtered with each of celite and silica. The reaction solution was concentrated and flash columned to synthesize Chemical Formula 1-3-a.

(2) Preparation of Chemical Formula 1-3-b

To Chemical Formula 1-3-a (3 g, 6.75 mmol) and potassium carbonate (2.33 g, 16.8 mmol), dimethyl formamide (DMF, 150 ml) was introduced for dissolution. After stirring the result for approximately 30 minutes at 60° C., perfluoro-1,1'-biphenyl (22.5 g, 67.5 mmol) was introduced thereto, the result was stirred for approximately 4 hours after raising the temperature to 90° C., and then the reaction temperature was lowered. Water was introduced thereto, and the organic layer was extracted using ethyl acetate and dried with $MgSO_4$. The reactant was concentrated and then flash columned to synthesize Chemical Formula 1-3-b.

(3) Preparation of Chemical Formula 1-3-c

To Chemical Formula 1-3-b (2.4 g, 2.23 mmol) and potassium carbonate (0.62 g, 4.46 mmol), DMF (25 ml) was introduced for dissolution. After stirring the result for approximately 30 minutes at 60° C., sodium-4-hydroxynaphthalene-2,7-disulfonate (1.7 g, 4.9 mmol) was introduced thereto, the result was stirred for approximately 18 hours after raising the temperature to 90° C., and then the reaction temperature was lowered. DMF (75 mL) was further introduced thereto, the result was filtered to remove salts, and filtration was repeated until portions insoluble in methanol disappeared to synthesize Chemical Formula 1-3-c.

(4) Preparation of Chemical Formula 1-3

To Chemical Formula 1-3-c (1 g), water (30 ml) and methanol (10 ml) were introduced for dissolution, and the result was flowed into an ion exchange resin (650CDOWEX™ MONOSPHERE™ 650 C) to synthesize Chemical Formula 1-3.

FIG. 4 is a diagram showing an MS spectrum of Chemical Formula 1-3.

<Preparation Example 1-4>—Preparation of Chemical Formula 1-4
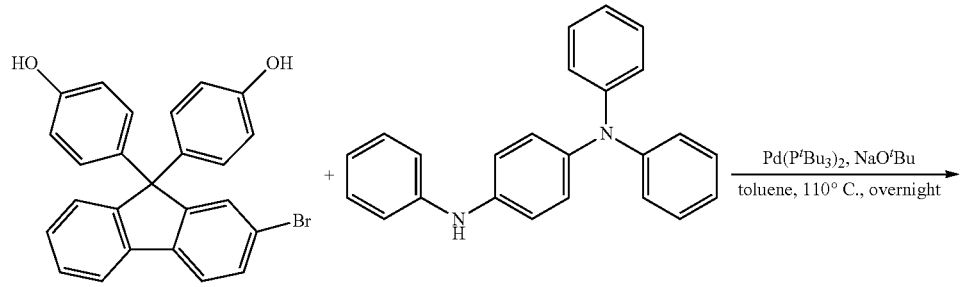
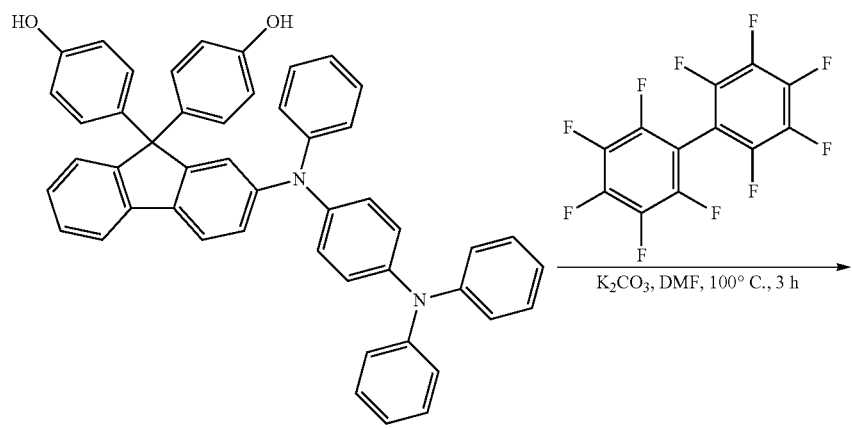
1-4-a
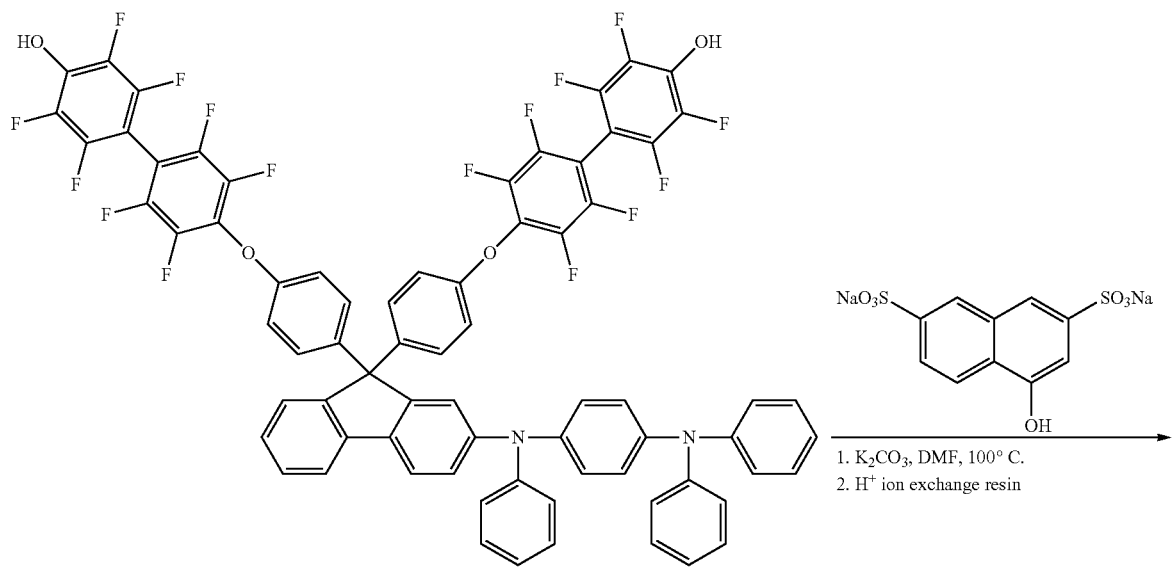
1-4-b

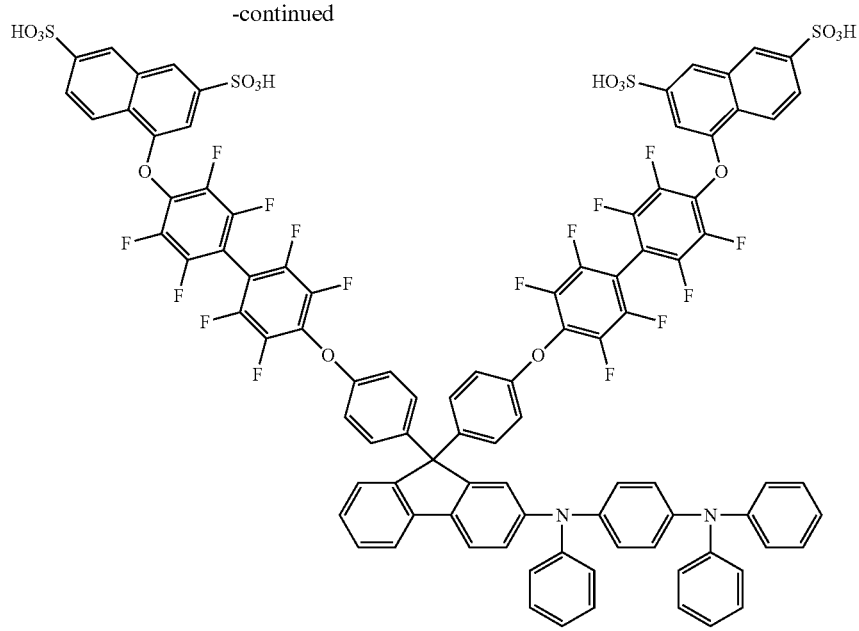

1-4

(1) Preparation of Chemical Formula 1-4-a

To 4,4'-(2-bromo-9H-fluorene-9,9-diyl)diphenol (3.00 g, 6.99 mmol), triphenylamine (2.59 g, 7.68 mmol) and NaOtBu (3.36 g, 34.9 mmol), degassed toluene and tetrahydrofuran (THF) were added in 200 mL and 50 mL, respectively, for dissolution under nitrogen atmosphere. The temperature was raised to 60° C., and after mixing the result for approximately 30 minutes, bis(tri-tert-butylphosphine)palladium ($Pd(PtBu_3)_2$, (0.18 g, 0.35 mmol) dissolved in THF was introduced thereto, and the result was reacted for approximately 18 hours. The temperature was lowered to room temperature, the solvent was removed, and the organic layer was extracted several times with $CH_2Cl_2/H_2O$. The result was dried with $MgSO_4$, and after adsorbing palladium, the result was filtered with each of celite and silica. The reaction solution was concentrated and flash columned to synthesize Compound 1-4-a.

(2) Preparation of Chemical Formula 1-4-b

To Chemical Formula 1-4-a (1.00 g, 1.46 mmol), perfluoro-1,1'-biphenyl (4.88 g, 14.6 mmol) and potassium carbonate (0.30 g, 2.19 mmol), DMF (50 ml) was introduced for dissolution. After that, the result was stirred for approximately 3 hours at 100° C. After lowering the reaction temperature, excess water was introduced thereto, and the organic layer was extracted using ethyl acetate and dried with $MgSO_4$. The reactant was concentrated and then flash columned to synthesize Chemical Formula 1-4-b.

(3) Preparation of Chemical Formula 1-4

To Chemical Formula 1-4-b (0.41 g, 0.31 mmol), sodium-4-hydroxynaphthalene-2,7-disulfonate (0.33 g, 0.94 mmol) and potassium carbonate (0.04 g, 0.31 mmol), DMF (10 mL) was introduced for dissolution. After that, the result was stirred for approximately 5 hours at 100° C. to progress a reaction. After lowering the reaction temperature, DMF (75 mL) was further introduced thereto, the result was filtered to remove salts, and filtration was repeated until portions insoluble in methanol disappeared to synthesize a metal salt intermediate. To this intermediate (0.50 g), water (30 ml) and methanol (10 ml) were introduced for dissolution, and the result was flowed into an ion exchange resin (650CDOWEX™ MONOSPHERE™ 650 C) having a volume of approximately 100 mL to synthesize Chemical Formula 1-4.

FIG. 5 is a diagram showing an MS spectrum of Chemical Formula 1-4.

<Preparation Example 1-5>—Preparation of Chemical Formula 1-5

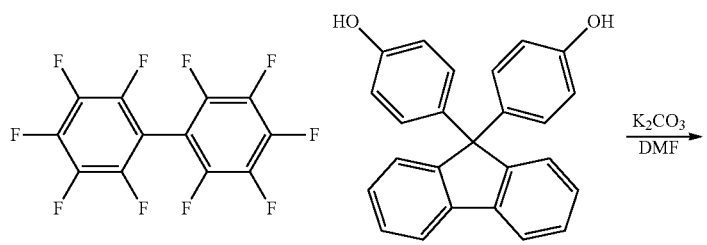

37
38
-continued
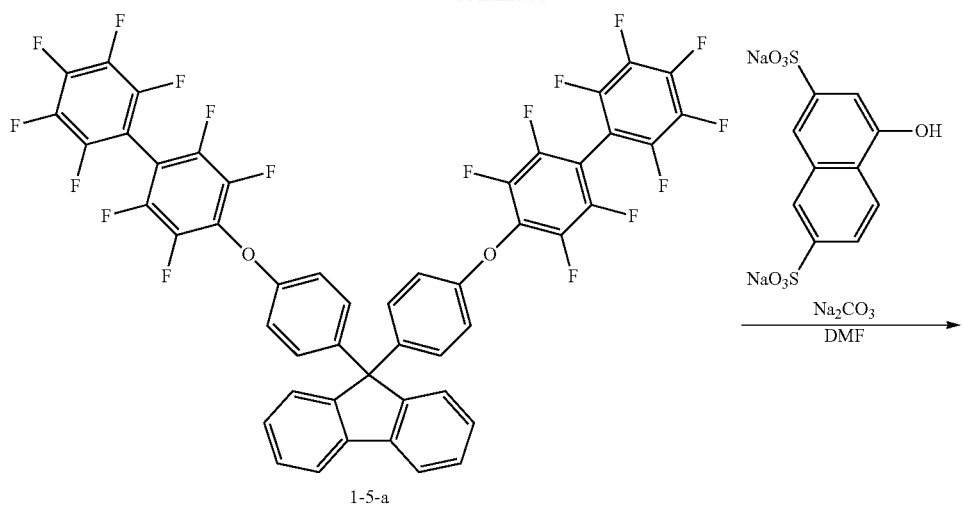
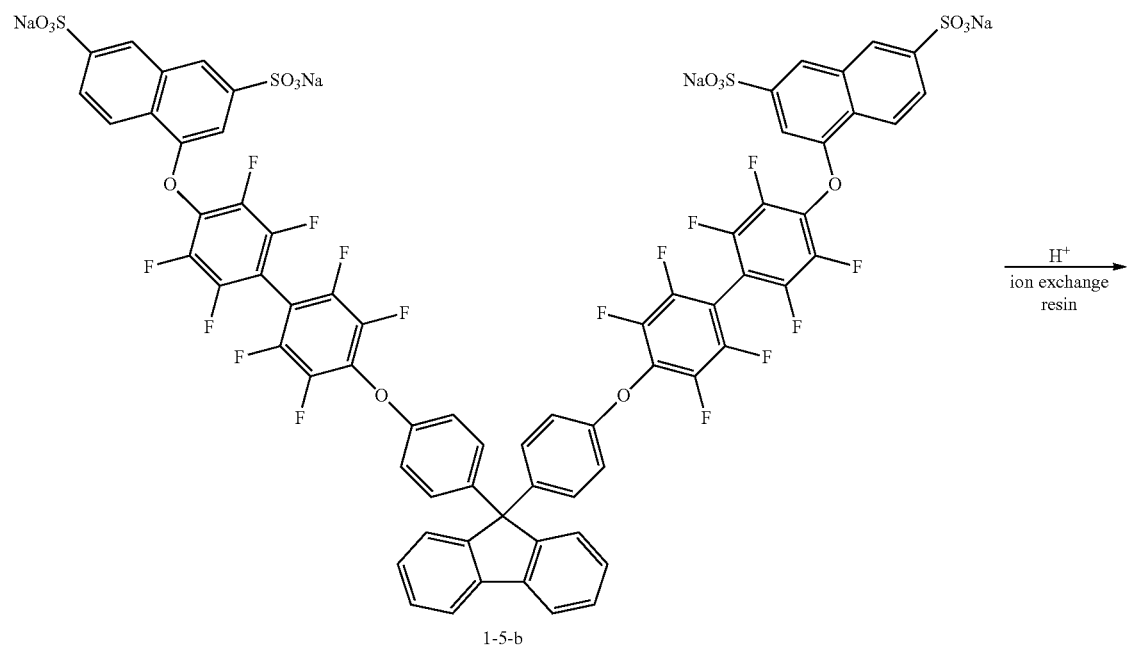

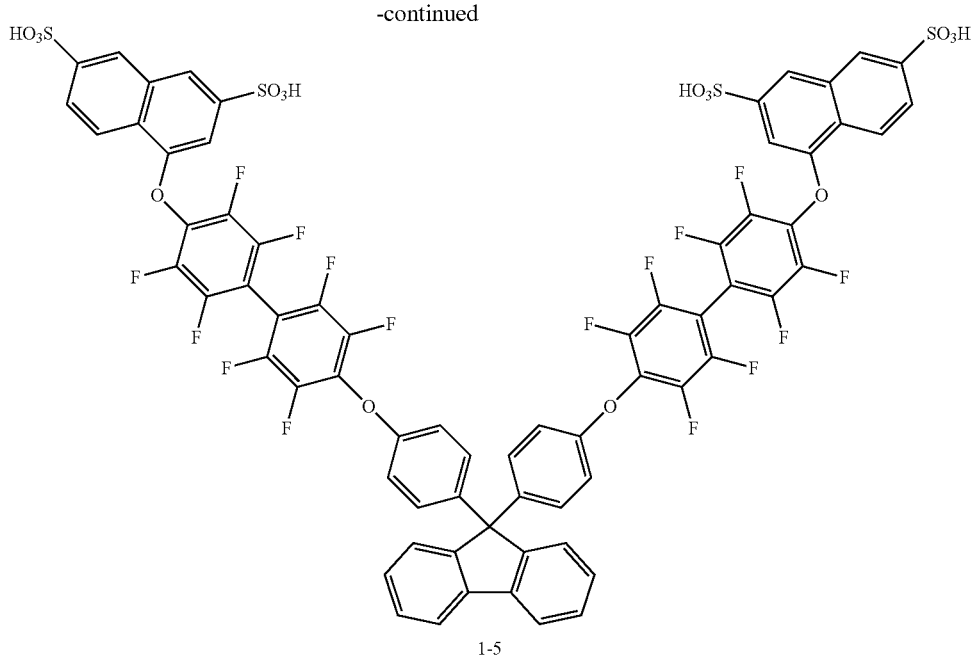

1-5

(1) Preparation of Chemical Formula 1-5-a

After dissolving decafluorophenyl (9.53 g), 4,4'-(9H-fluorene-9,9-diyl)diphenol (1 g) and potassium carbonate (788 mg) in DMF (28 ml), the result was reacted for 14 hours at 100° C., and then washed and extracted using ethyl acetate and water, dried with MgSO$_4$, vacuumed, and then column chromatographed to synthesize Chemical Formula 1-5-a.

(2) Preparation of Chemical Formula 1-5-b

After dissolving Chemical Formula 1-5-a (1.5 g) and 1-naphthol-3,6-disulfonic acid disodium salt (1.235 g) and sodium carbonate (341 mg) in DMF (15 ml) and reacting the result for 24 hours at 100° C., this was dissolved DMF (300 ml), filtered to remove solids, and vacuumed to remove DMF. After dissolving the result in methanol, a filtering process was repeated 5 times. For the obtained solids, additional impurities were removed using methylene chloride, and the result was dried to synthesize Chemical Formula 1-5-b.

(3) Preparation of Chemical Formula 1-5

After dissolving Chemical Formula 1-5-b (300 mg) in water (10 g), the result passed through an ion exchange resin to exchange Na with H. The water obtained herein was removed under vacuum to obtain Chemical Formula 1-5.

FIG. 6 is a diagram showing an MS spectrum of Chemical Formula 1-5.

<Preparation Example 1-6>—Preparation of Chemical Formula 2-1

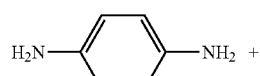

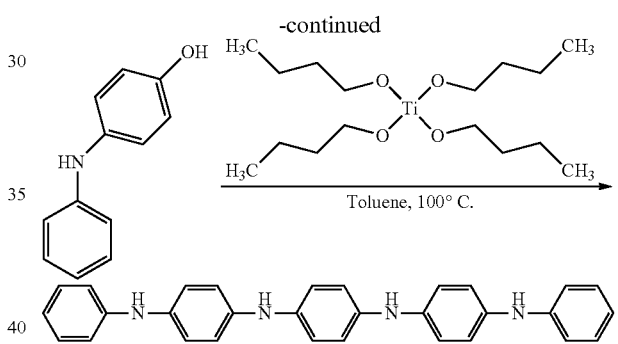

After dissolving p-phenylenediamine (2 g, 18.5 mmol) in toluene (308 ml) and adding tetra-n-butoxy titanium thereto, the result was heated to 70° C. and stirred. p-Hydroxydiphenylamine (8.15 g, 44.4 mmol) was added thereto, and the result was reacted for 24 hours at 100° C. under nitrogen atmosphere. After terminating the reaction, the reaction solution was filtered, washed consecutively with toluene and ether, and then dried to obtain silver crystals. With respect to the obtained crystals, dioxane anhydrous in a weight ratio of 25 times and hydrazine monohydrate in a weight ratio of 0.2 times mol were added, and after replacing the reaction system with nitrogen and heating under reflux, the crystals were dissolved. Toluene was introduced to the obtained solution to suspend the solution, and after heating under reflux, the result was filtered to obtain solids. The solids precipitated from the bare solution were recrystallized with toluene:dioxane=1:1 under nitrogen atmosphere, and washed consecutively with ether to obtain light grey solids. The recrystallization process was repeated to obtain more purified Chemical Formula 2-1.

FIG. 7 is a diagram showing an MS spectrum of Chemical Formula 2-1.

<Preparation Example 1-7>—Preparation of Chemical Formula 2-2

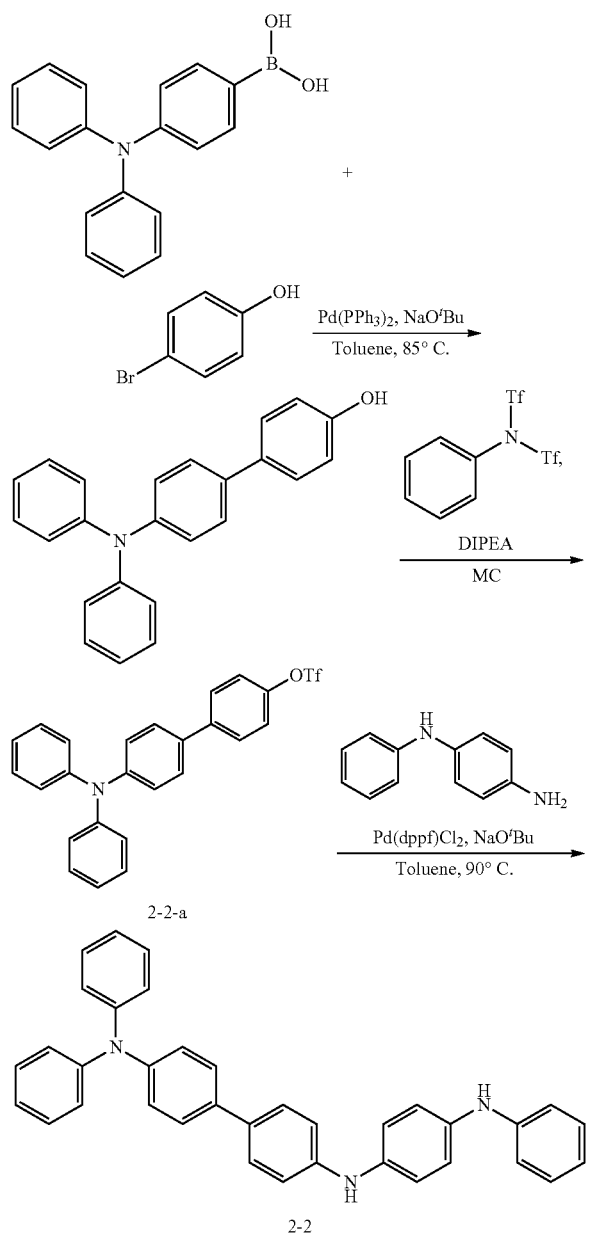

(1) Preparation of Chemical Formula 2-2-a

After dissolving 4-(diphenylamino)phenylboronic acid (2.46 g, 8.89 mmol) in methylene chloride (25 ml), diisopropylamine (3.2 ml, 22.23 mmol) was added thereto, and the result was stirred after adjusting the temperature to 0° C. After 30 minutes, N-phenyl-bis(trifluoromethanesulfonimide) (5.2 g, 17.78 mmol) was slowly added thereto. After that, the result was kept stirred while slowly raising the temperature to room temperature. The reaction was terminated after 1 hour, water was added thereto, and then methylene chloride was added subsequently. The result was washed with $H_2O$ and brine, the organic solvent was separated and dried with $MgSO_4$. After that, the filtrate was filtered with celite and silica. Chemical Formula 2-2-a was obtained through column chromatography.

(2) Preparation of Chemical Formula 2-2

To amine (2.55 g, 5.43 mmol), [1,1'-bis(diphenylphosphino)ferrocene]dichloropalladium(II) (119 mg, 0.163 mmol) and sodium tert-butoxide (1.8 g, 19 mmol), methylene chloride (18 ml) was introduced for dissolution. The result was heated to 90° C. and stirred under nitrogen atmosphere. After 30 minutes, a triflate reagent (1 g, 5.43 mmol) dissolved in methylene chloride was slowly added thereto. When the reaction was terminated after stirring the result for 1 hours and 30 minutes, the result went through workup using ethyl acetate and water. The mixture was washed with brine, and the organic layer was separated and dried with $MgSO_4$. After treating the result with activated carbon, filtration was progressed. After that, the solvent of the filtrate was removed using a vacuum evaporator, and the result was purified through column chromatography. The material was separated from impurities using an eluent of EA/HEX 5%, and after re-columned using an eluent of MC/HEX 50%, colors of the material were removed. Chemical Formula 2-2, a solid material in pink, was obtained in an approximately 5% yield (80 mg).

FIG. 8 is a diagram showing an MS spectrum of Chemical Formula 2-2.

<Preparation Example 2>—Preparation of Coating Composition

Preparation Example 2-1

Chemical Formula 2-1 and Chemical Formula 1-1 were dissolved in dimethylacetamide in a ratio of 1:4 to prepare a 2 wt % solution of Coating Composition 1.

Preparation Example 2-2

Chemical Formula 2-1 and Chemical Formula 1-2 were dissolved in dimethylacetamide in a ratio of 1:4 to prepare a 2 wt % solution of Coating Composition 2.

Preparation Example 2-3

Chemical Formula 2-1 and Chemical Formula 1-4 were dissolved in dimethylacetamide in a ratio of 1:4 to prepare a 2 wt % solution of Coating Composition 3.

Preparation Example 2-4

Chemical Formula 2-1 and Chemical Formula 1-5 were dissolved in dimethylacetamide in a ratio of 1:4 to prepare a 2 wt % solution of Coating Composition 4.

Preparation Example 2-5

Chemical Formula 2-2 and Chemical Formula 1-2 were dissolved in dimethylacetamide in a ratio of 1:4 to prepare a 2 wt % solution of Coating Composition 5.

Preparation Example 2-6

Chemical Formula 2-2 and Chemical Formula 1-5 were dissolved in dimethylacetamide in a ratio of 1:4 to prepare a 2 wt % solution of Coating Composition 6.

Comparative Example 2-1

Chemical Formula 2-1 and the following Compound D1 were dissolved in dimethylacetamide in a ratio of 1:4 to prepare a 2 wt % solution of Coating Composition 7.

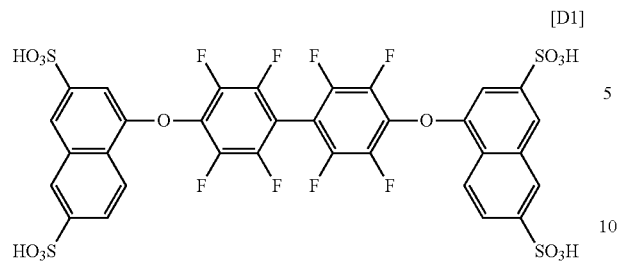

[D1]

Comparative Example 2-2

Chemical Formula 2-2 and Compound D1 were dissolved in dimethylacetamide in a ratio of 1:4 to prepare a 2 wt % solution of Coating Composition 8.

Comparative Example 2-3

Chemical Formula 2-2 and the following Compound D2 were dissolved in dimethylacetamide in a ratio of 1:4 to prepare a 2 wt % solution of Coating Composition 9.

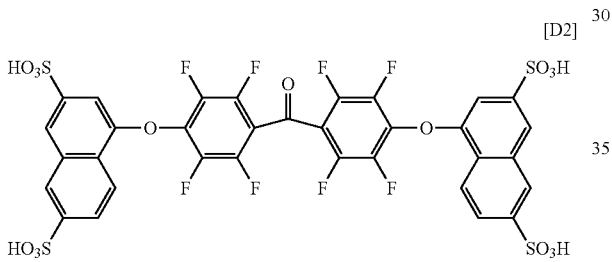

[D2]

<Example>—Manufacture of Organic Light Emitting Device

Example 1

A glass substrate on which indium tin oxide (ITO) was deposited as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone for 30 minutes each, dried, and then transferred to a glove box.

On the substrate prepared as above, a hole injection layer was formed by coating Coating Composition 1 to a thickness of 300 Å through spin coating, and heat treating the coating composition for 30 minutes at 230° C. under nitrogen atmosphere. After that, a hole transfer layer was formed on the hole injection layer by dissolving the following Compound HT-1 in toluene in 1 wt/v % and then spin coating the result.

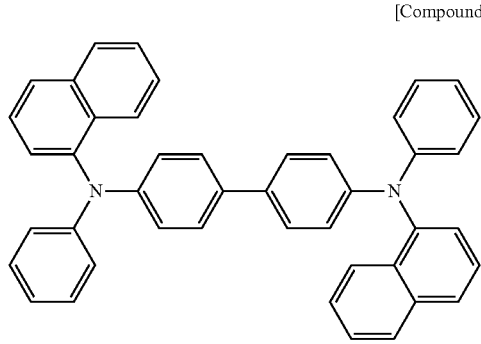

[Compound HT-1]

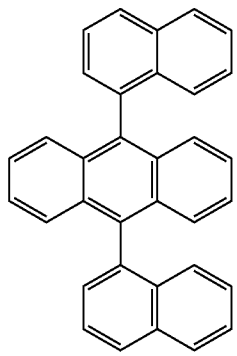

[Compound EM-1]

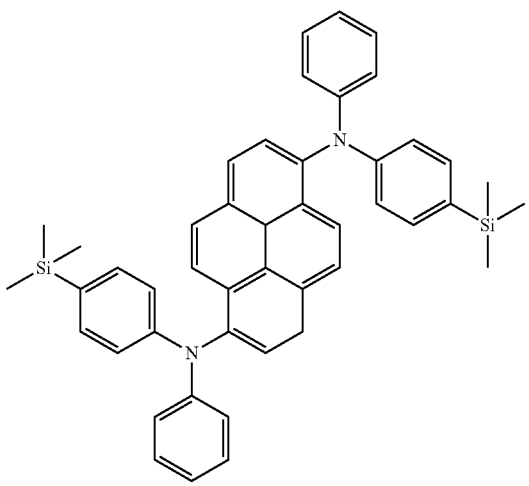

[Compound EM-2]

-continued

[Compound ET-1]

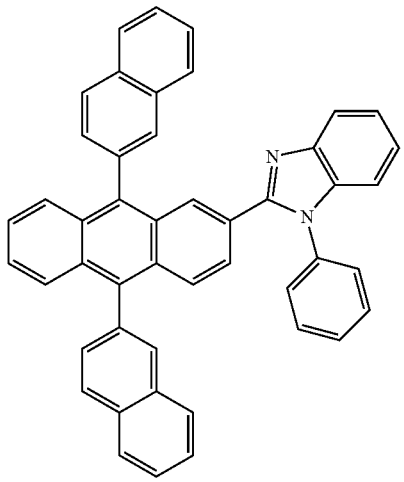

Subsequently, the result was transferred to a vacuum depositor, and a light emitting layer was formed on the hole transfer layer by vacuum depositing Compound EM-1 and Compound EM-2 to a thickness of 200 Å in a ratio of 0.92:0.08. On the light emitting layer, Compound ET-1 was vacuum deposited to a thickness of 350 Å to form an electron injection and transfer layer. A cathode was formed on the electron injection and transfer layer by depositing LiF to a thickness of 12 Å and aluminum to a thickness of 2,000 Å in consecutive order.

In the above-mentioned processes, the deposition rates of the organic materials were maintained at 0.4 Å/sec to 0.7 Å/sec, the deposition rates of the LiF and the aluminum of the cathode were maintained at 0.3 Å/sec and 2 Å/sec, respectively, and the degree of vacuum during the deposition was maintained at $2\times10^{-7}$ to $5\times10^{-8}$ torr.

After that, sealing was conducted by bonding sealing glass and the substrate to glass using a photocurable epoxy resin to manufacture an organic light emitting device having a multilayer structure. Subsequent operations were conducted at room temperature (25° C.) in the atmosphere.

Example 2

An organic light emitting device was manufactured in the same manner as in Example 1 except that Coating Composition 2 was used instead of Coating Composition 1.

Example 3

An organic light emitting device was manufactured in the same manner as in Example 1 except that Coating Composition 3 was used instead of Coating Composition 1.

Example 4

An organic light emitting device was manufactured in the same manner as in Example 1 except that Coating Composition 4 was used instead of Coating Composition 1.

Example 5

An organic light emitting device was manufactured in the same manner as in Example 1 except that Coating Composition 5 was used instead of Coating Composition 1.

Example 6

An organic light emitting device was manufactured in the same manner as in Example 1 except that Coating Composition 6 was used instead of Coating Composition 1.

Comparative Example 1

An organic light emitting device was manufactured in the same manner as in Example 1 except that Coating Composition 7 was used instead of Coating Composition 1.

Comparative Example 2

An organic light emitting device was manufactured in the same manner as in Example 1 except that Coating Composition 8 was used instead of Coating Composition 1.

Comparative Example 3

An organic light emitting device was manufactured in the same manner as in Example 1 except that Coating Composition 9 was used instead of Coating Composition 1.

Voltage, efficiency, color coordinate and lifetime were measured when applying a current to each of the organic light emitting devices manufactured in Examples 1 to 6 and Comparative Examples 1 to 3, and the results are shown in the following [Table 1] and [Table 2]. T90 means time taken for the luminance decreasing to 90% compared to its initial luminance, and T95 means time taken for the luminance decreasing to 95% compared to its initial luminance.

TABLE 1

| Experimental Results | Coating Composition | Volt (V) | QE (%) | CIEx | CIEy | T90 (hr) |
|---|---|---|---|---|---|---|
| Example 1 | Coating Composition 1 | 4.21 | 4.68 | 0.136 | 0.106 | 71 |
| Example 2 | Coating Composition 2 | 4.33 | 4.64 | 0.135 | 0.116 | 135 |
| Example 3 | Coating Composition 3 | 4.58 | 4.70 | 0.137 | 0.105 | 90 |
| Example 4 | Coating Composition 4 | 4.23 | 4.92 | 0.137 | 0.105 | 68 |
| Comparative Example 1 | Coating Composition 7 | 4.35 | 4.42 | 0.137 | 0.105 | 45 |

As shown in Table 1, it was seen that the organic light emitting device manufactured using the coating composition comprising the compound represented by Chemical Formula 1 and the compound represented by Chemical Formula 2 of the present specification as a hole injection layer exhibited long lifetime properties compared to Comparative Example 1.

TABLE 2

| Experimental Results | Coating Composition | Volt (V) | QE (%) | CIEx | CIEy | T95 (hr) |
|---|---|---|---|---|---|---|
| Example 5 | Coating Composition 5 | 4.95 | 4.32 | 0.137 | 0.117 | 141 |
| Example 6 | Coating Composition 6 | 4.70 | 4.66 | 0.136 | 0.114 | 82 |
| Comparative Example 2 | Coating Composition 8 | 4.76 | 4.34 | 0.137 | 0.114 | 42 |
| Comparative Example 3 | Coating Composition 9 | 4.32 | 4.41 | 0.137 | 0.116 | 67 |

As shown in Table 2, it was seen that the organic light emitting device manufactured using the coating composition comprising the compound represented by Chemical Formula 1 and the compound represented by Chemical Formula 2 of the present specification as a hole injection layer exhibited long lifetime properties compared to Comparative Examples 2 and 3.

Hereinbefore, preferred experimental examples (hole injection layer) of the present disclosure have been described, however, the present disclosure is not limited thereto, and various modifications may be made within the scope of the claims and detailed descriptions of the disclosure, and these also fall within the category of the disclosure.

REFERENCE NUMERAL

101: Substrate
201: Anode
301: Hole Injection Layer
401: Hole Transfer Layer
501: Light Emitting Layer
601: Electron Transfer Layer
701: Cathode

The invention claimed is:

1. A coating composition comprising:
a compound represented by the following Chemical Formula 1; and
a compound represented by the following Chemical Formula 2:

[Chemical Formula 1]

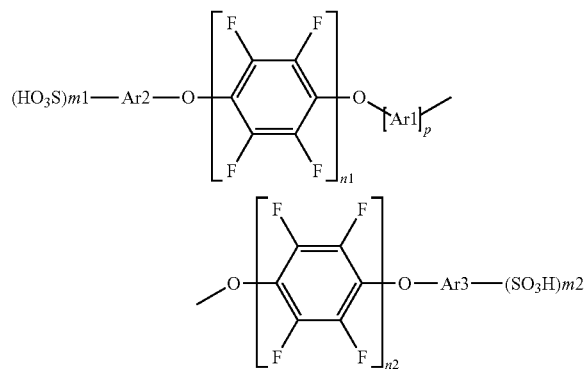

in Chemical Formula 1,
Ar1 is a substituted or unsubstituted alkylene group; a substituted or unsubstituted divalent carbonyl group; a substituted or unsubstituted divalent amine group; or a substituted or unsubstituted arylene group;
Ar2 and Ar3 are the same as or different from each other, and each independently a substituted or unsubstituted arylene group;
m1, m2, n1 and n2 are the same as or different from each other, and each independently an integer of 1 to 10;
p is an integer of 2 to 10, and Ar1s are the same as or different from each other,

[Chemical Formula 2]

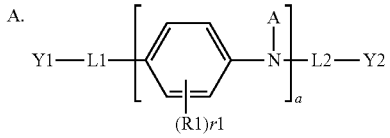

in Chemical Formula 2,
L1 and L2 are the same as or different from each other, and each independently a direct bond; a substituted or unsubstituted arylene group; or a substituted or unsubstituted heteroarylene group;
A, R1, Y1 and Y2 are the same as or different from each other, and each independently hydrogen; deuterium; a substituted or unsubstituted alkyl group; a substituted or unsubstituted cycloalkyl group; a substituted or unsubstituted amine group; a substituted or unsubstituted aryl group; or a substituted or unsubstituted heterocyclic group;
a is an integer of 1 to 10;
when a is 2 or greater, each of

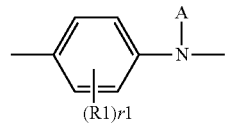

is the same as or different from each other;
r1 is an integer of 1 to 4; and
when r1 is 2 or greater, R1s are the same as or different from each other.

2. The coating composition of claim 1, wherein (m1+m2)/(n1+n2)≤1.

3. The coating composition of claim 1, wherein Ar1 is selected from among the following A-1 to A-5:

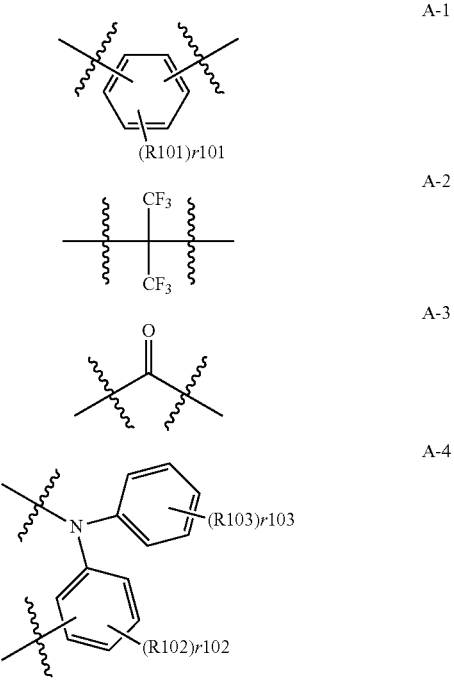

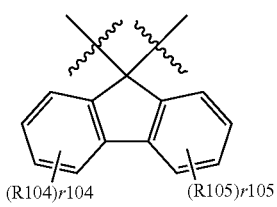
A-5 in the A-1 to A-5,

R101 to R105 are the same as or different from each other, and each independently hydrogen; deuterium; a halogen group; a nitrile group; a substituted or unsubstituted alkyl group; a substituted or unsubstituted cycloalkyl group; a substituted or unsubstituted amine group; a substituted or unsubstituted aryl group; or a substituted or unsubstituted heterocyclic group;

r101, r102, r104 and r105 are each independently an integer of 1 to 4;

r103 is an integer of 1 to 5; and when r101 to r105 are each 2 or greater, R101s to R105s are each independently the same as or different from each other.

4. The coating composition of claim 1, wherein —[Ar1]p- is selected from among the following A-11 to A-15:

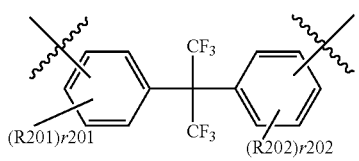
A-11

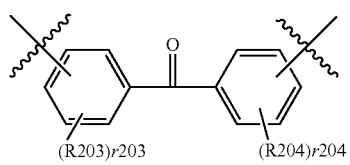
A-12

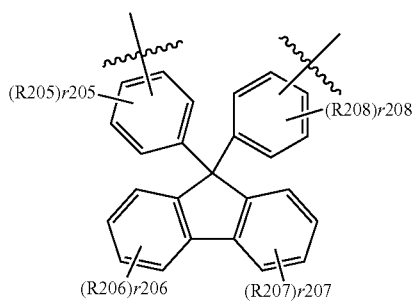
A-13

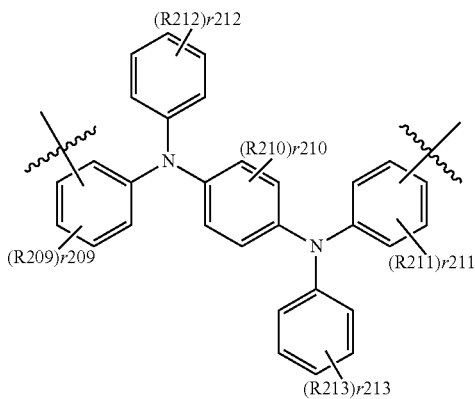
A-14

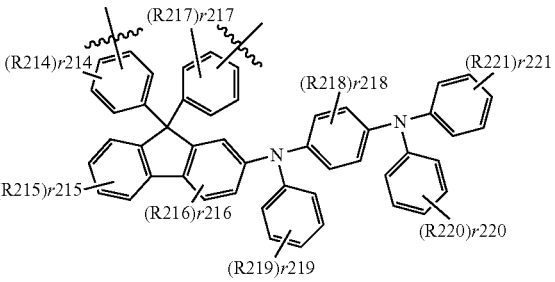
A-15 in the A-11 to A-15,

R201 to R221 are the same as or different from each other, and each independently hydrogen; deuterium; a halogen group; a nitrile group; a substituted or unsubstituted alkyl group; a substituted or unsubstituted cycloalkyl group; a substituted or unsubstituted amine group; a substituted or unsubstituted aryl group; or a substituted or unsubstituted heterocyclic group;

r201 to r211, r214, r215, r217 and r218 are each independently an integer of 1 to 4;

r212, r213 and r219 to r221 are each independently an integer of 1 to 5;

r216 is an integer of 1 to 3; and when r201 to r221 are each 2 or greater, R201s to R221s are each independently the same as or different from each other.

5. The coating composition of claim 1, wherein the compound represented by Chemical Formula 1 is selected from among the following Chemical Formula 1-1 to Chemical Formula 1-5:

[Chemical Formula 1-1]

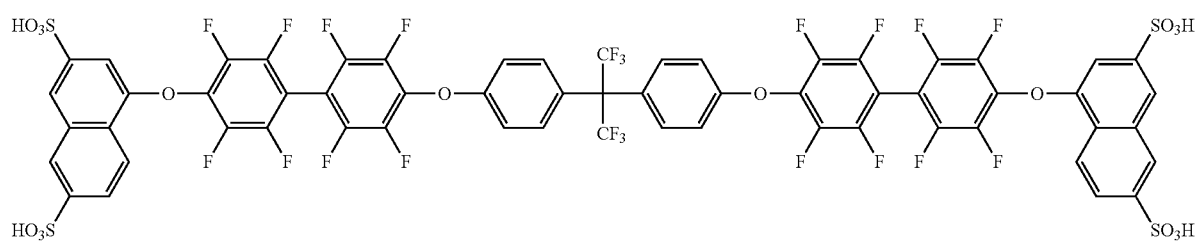

-continued
[Chemical Formula 1-2]
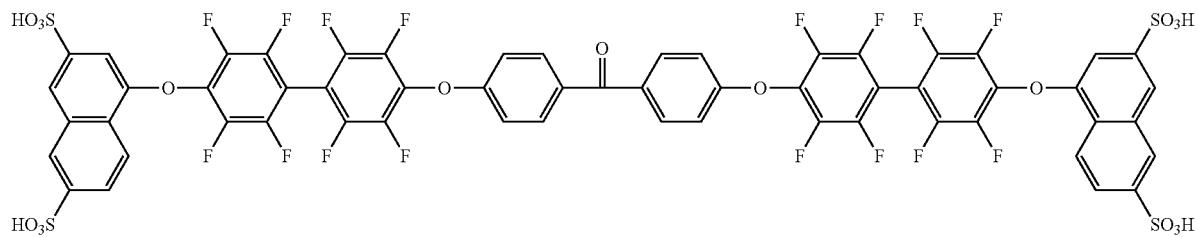
[Chemical Formula 1-3]
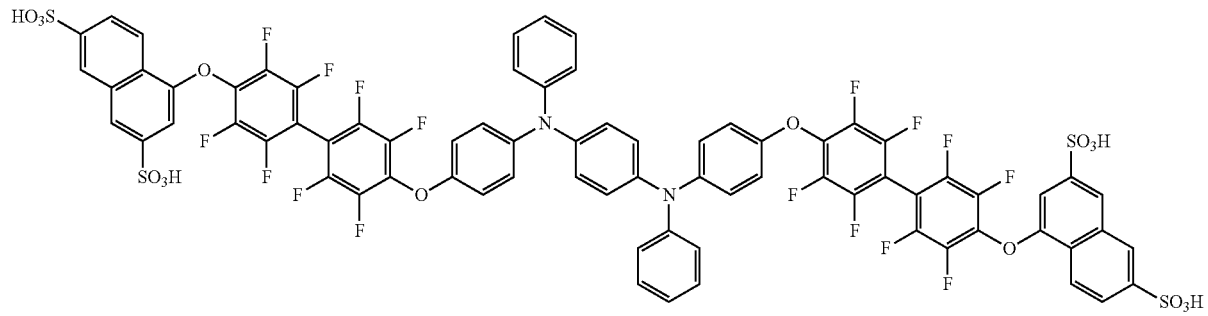
[Chemical Formula 1-4]
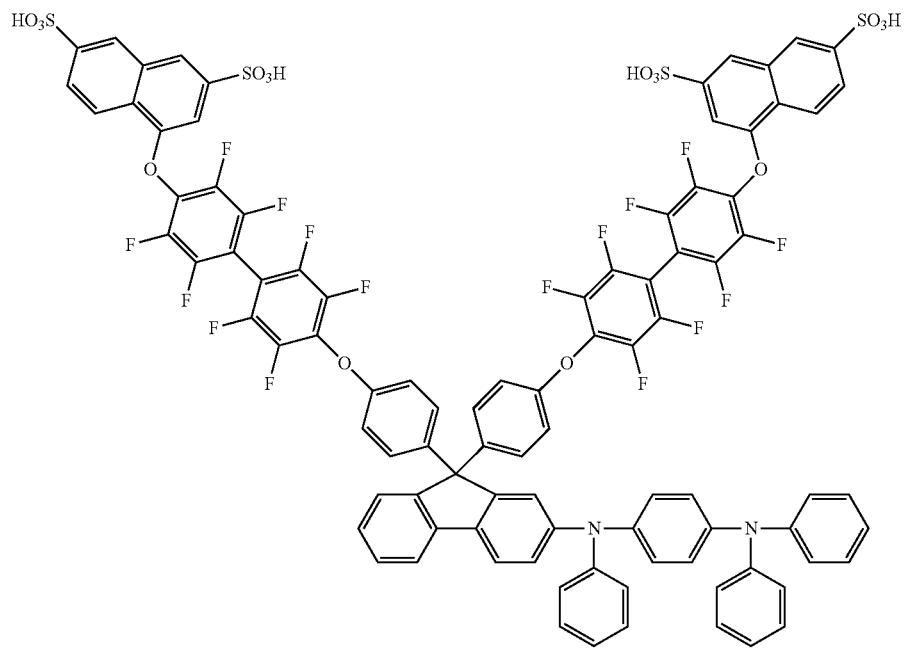

[Chemical Formula 1-5]

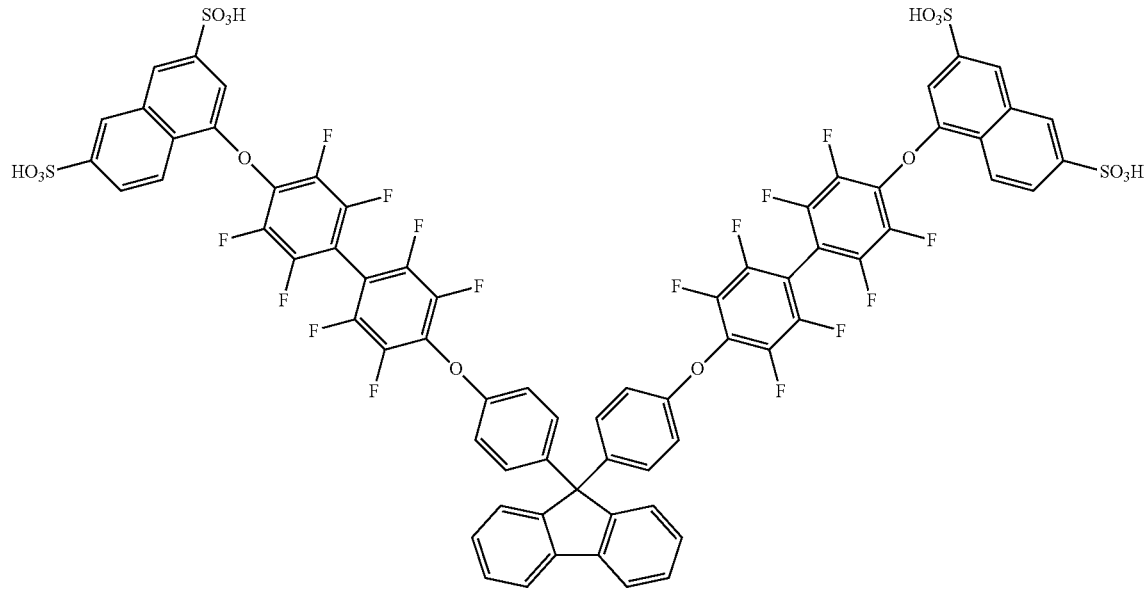

6. The coating composition of claim 1, wherein the compound represented by Chemical Formula 2 is the following Chemical Formula 2-1 or Chemical Formula 2-2:

[Chemical Formula 2-1]

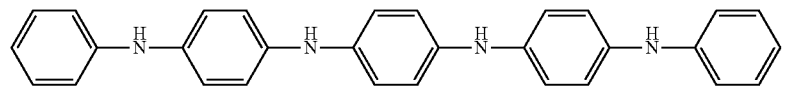

[Chemical Formula 2-2]

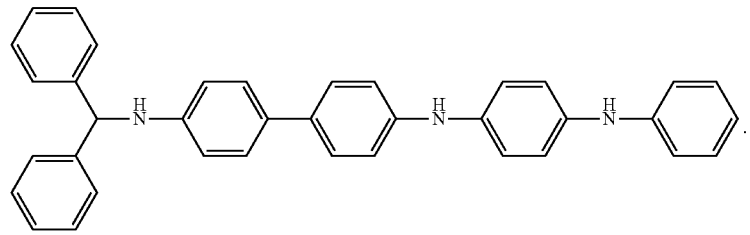

7. An organic light emitting device comprising:
a first electrode;
a second electrode provided opposite to the first electrode; and
one or more organic material layers provided between the first electrode and the second electrode,
wherein the one or more layers of the organic material layers comprise the coating composition of claim 1.

8. The organic light emitting device of claim 7, wherein the organic material layer comprises a hole transfer layer, a hole injection layer, or a layer carrying out hole transfer and hole injection at the same time, and the hole transfer layer, the hole injection layer, or the layer carrying out hole transfer and hole injection at the same time comprises the coating composition.

9. A method for manufacturing an organic light emitting device comprising:
preparing a substrate;
forming a first electrode on the substrate;
forming one or more organic material layers on the first electrode; and
forming a second electrode on the organic material layers,
wherein the forming of the one or more organic material layers comprises forming the one or more material layers using the coating composition of claim 1.

10. The method for manufacturing an organic light emitting device of claim 9, wherein the one or more organic material layers formed using the coating composition is formed by using spin coating or ink jetting.

11. The coating composition of claim 1, further comprising a solvent.

12. The coating composition of claim 11, where the solvent comprises chlorine-based solvents, ether-based solvents, aromatic hydrocarbon-based solvents, aliphatic hydrocarbon-based solvents, ketone-based solvents, ester-based solvents, polyalcohols, alcohol-based solvents, sulfoxide-based solvents, amide-based solvents, benzoate-based solvents, tetraline, or a combination thereof.

13. The coating composition of claim 1, wherein a concentration of the compound represented by Chemical Formula 1 and the compound represented by Chemical Formula 2 is 0.1 wt/v % to 20 wt/v %.

14. The method for manufacturing an organic light emitting device of claim 9, wherein the one or more organic material layers formed using the coating composition is formed by heat treatment or light treatment.

* * * * *